(12) United States Patent
Park et al.

(10) Patent No.: US 10,295,908 B2
(45) Date of Patent: May 21, 2019

(54) BLOCK COPOLYMER

(71) Applicant: LG Chem, Ltd., Seoul (KR)

(72) Inventors: No Jin Park, Daejeon (KR); Jung Keun Kim, Daejeon (KR); Je Gwon Lee, Daejeon (KR); Sung Soo Yoon, Daejeon (KR); Se Jin Ku, Daejeon (KR); Mi Sook Lee, Daejeon (KR); Eun Young Choi, Daejeon (KR); Hyung Ju Ryu, Daejeon (KR)

(73) Assignee: LG Chem, Ltd. (KR)

( * ) Notice: Subject to any disclaimer, the term of this patent is extended or adjusted under 35 U.S.C. 154(b) by 111 days.

(21) Appl. No.: 15/515,290

(22) PCT Filed: Sep. 30, 2015

(86) PCT No.: PCT/KR2015/010323
§ 371 (c)(1),
(2) Date: Mar. 29, 2017

(87) PCT Pub. No.: WO2016/053001
PCT Pub. Date: Apr. 7, 2016

(65) Prior Publication Data
US 2017/0226235 A1    Aug. 10, 2017

(30) Foreign Application Priority Data

Sep. 30, 2014  (KR) .................. 10-2014-0131964
Jun. 4, 2015   (KR) .................. 10-2015-0079480

(51) Int. Cl.
*C08F 32/06*       (2006.01)
*G03F 7/16*        (2006.01)
(Continued)

(52) U.S. Cl.
CPC ............. *G03F 7/165* (2013.01); *B05D 1/005* (2013.01); *B05D 3/007* (2013.01);
(Continued)

(58) Field of Classification Search
CPC ........ C08F 212/08; C08F 32/06; C08L 53/00; C08L 53/005; B81C 1/00428; B81C 2201/0149; C09D 153/00
See application file for complete search history.

(56) References Cited

U.S. PATENT DOCUMENTS 3,976,672 A    8/1976  Strunk et al.
5,115,056 A    5/1992  Mueller et al.
(Continued)

FOREIGN PATENT DOCUMENTS

CN    1333790 A    1/2002
CN    1337974 A    2/2002
(Continued)

OTHER PUBLICATIONS

Kobayashi et al Macromolecules, 39, 18, 5979-5986 (Year: 2006).*
(Continued)

*Primary Examiner* — Mark S Kaucher
(74) *Attorney, Agent, or Firm* — Lerner, David, Littenberg, Krumholz & Mentlik, LLP

(57) ABSTRACT

The present application relates to a monomer, a method for preparing a block copolymer, a block copolymer, and uses thereof. Each monomer of the present application exhibits an excellent self-assembling property and is capable of forming a block copolymer to which a variety of required functions are granted as necessary without constraint.

16 Claims, 2 Drawing Sheets

(51) Int. Cl.

| | | |
|---|---|---|
| *C08G 61/12* | (2006.01) | |
| *H01L 21/3105* | (2006.01) | |
| *H01L 21/027* | (2006.01) | |
| *C08F 212/08* | (2006.01) | |
| *C08F 216/12* | (2006.01) | |
| *C08F 220/10* | (2006.01) | |
| *C08F 220/26* | (2006.01) | |
| *C08F 220/30* | (2006.01) | |
| *C08J 5/18* | (2006.01) | |
| *C08L 53/00* | (2006.01) | |
| *B05D 1/00* | (2006.01) | |
| *B05D 3/00* | (2006.01) | |
| *C08F 293/00* | (2006.01) | |
| *C09D 153/00* | (2006.01) | |
| *G03F 7/09* | (2006.01) | |
| *G03F 7/004* | (2006.01) | |
| *G03F 7/039* | (2006.01) | |
| *G03F 7/20* | (2006.01) | |
| *C08F 299/02* | (2006.01) | |
| *C08G 61/08* | (2006.01) | |
| *C08F 2/14* | (2006.01) | |
| *C08J 7/12* | (2006.01) | |
| *G03F 7/00* | (2006.01) | |
| *G03F 7/30* | (2006.01) | |
| *C08L 53/02* | (2006.01) | |
| *B81C 1/00* | (2006.01) | |
| *B82Y 40/00* | (2011.01) | |

(52) U.S. Cl.
CPC ............ *B81C 1/00428* (2013.01); *C08F 2/14* (2013.01); *C08F 32/06* (2013.01); *C08F 212/08* (2013.01); *C08F 216/12* (2013.01); *C08F 220/10* (2013.01); *C08F 220/26* (2013.01); *C08F 220/30* (2013.01); *C08F 293/00* (2013.01); *C08F 293/005* (2013.01); *C08F 299/024* (2013.01); *C08G 61/08* (2013.01); *C08G 61/12* (2013.01); *C08J 5/18* (2013.01); *C08J 7/123* (2013.01); *C08L 53/00* (2013.01); *C08L 53/005* (2013.01); *C08L 53/02* (2013.01); *C09D 153/00* (2013.01); *G03F 7/0002* (2013.01); *G03F 7/0046* (2013.01); *G03F 7/039* (2013.01); *G03F 7/091* (2013.01); *G03F 7/16* (2013.01); *G03F 7/162* (2013.01); *G03F 7/2004* (2013.01); *G03F 7/30* (2013.01); *H01L 21/0273* (2013.01); *H01L 21/31055* (2013.01); *H01L 21/31056* (2013.01); *H01L 21/31058* (2013.01); *B81C 2201/0149* (2013.01); *B82Y 40/00* (2013.01); *C01P 2002/70* (2013.01); *C07B 2200/00* (2013.01); *C08F 2220/301* (2013.01); *C08F 2438/03* (2013.01); *C08G 2261/1424* (2013.01); *C08G 2261/1426* (2013.01); *C08G 2261/332* (2013.01); *C08G 2261/3324* (2013.01); *C08G 2261/40* (2013.01); *C08G 2261/418* (2013.01); *C08J 2353/00* (2013.01)

(56) References Cited

U.S. PATENT DOCUMENTS

| | | | |
|---|---|---|---|
| 5,202,402 | A | 4/1993 | Funaki et al. |
| 5,234,604 | A | 8/1993 | Liao et al. |
| 5,391,626 | A | 2/1995 | Machida et al. |
| 5,418,290 | A | 5/1995 | Machida et al. |
| 5,554,695 | A | 9/1996 | Machida et al. |
| 5,728,431 | A | 3/1998 | Bergbreiter et al. |
| 6,025,437 | A | 2/2000 | Hirahara et al. |
| 6,314,225 | B1 | 11/2001 | Wang |
| 6,531,547 | B1 | 3/2003 | Visger et al. |
| 6,546,282 | B1 | 4/2003 | Inoue et al. |
| 6,953,649 | B2 | 10/2005 | Prat et al. |
| 7,538,159 | B2 | 5/2009 | Wang et al. |
| 8,163,189 | B2 | 4/2012 | Iyoda et al. |
| 8,211,737 | B2 | 7/2012 | Russell et al. |
| 8,791,042 | B2 | 7/2014 | Ronan et al. |
| 9,495,991 | B2 | 11/2016 | Han et al. |
| 2003/0143343 | A1 | 7/2003 | Kawabata et al. |
| 2004/0049836 | A1 | 3/2004 | Ashraf et al. |
| 2004/0110856 | A1 | 6/2004 | Young et al. |
| 2004/0143032 | A1 | 7/2004 | Auschra et al. |
| 2004/0242787 | A1 | 12/2004 | Chun et al. |
| 2006/0166033 | A1 | 7/2006 | Poetsch et al. |
| 2006/0172082 | A1 | 8/2006 | Masuda |
| 2007/0142559 | A1 | 6/2007 | Wang et al. |
| 2007/0166648 | A1 | 7/2007 | Ponoth et al. |
| 2007/0219338 | A1 | 9/2007 | Takeda et al. |
| 2008/0105854 | A1 | 5/2008 | Huh et al. |
| 2008/0193658 | A1 | 8/2008 | Millward |
| 2008/0213556 | A1 | 9/2008 | Cha et al. |
| 2008/0286333 | A1 | 11/2008 | Kangas et al. |
| 2008/0311402 | A1 | 12/2008 | Jung et al. |
| 2009/0114108 | A1 | 5/2009 | Oya et al. |
| 2009/0240001 | A1 | 9/2009 | Regner |
| 2009/0253867 | A1 | 10/2009 | Takahashi et al. |
| 2009/0306295 | A1 | 12/2009 | Mays et al. |
| 2010/0086801 | A1 | 4/2010 | Russell et al. |
| 2010/0098876 | A1 | 4/2010 | Hanson |
| 2010/0102415 | A1 | 4/2010 | Millward et al. |
| 2010/0120985 | A1 | 5/2010 | Konishi et al. |
| 2010/0155988 | A1 | 6/2010 | Keil et al. |
| 2010/0206057 | A1 | 8/2010 | Batchelder et al. |
| 2010/0210742 | A1 | 8/2010 | Iyoda et al. |
| 2010/0216312 | A1 | 8/2010 | Yamamoto et al. |
| 2010/0266957 | A1 | 10/2010 | Harada et al. |
| 2010/0285276 | A1 | 11/2010 | Kim et al. |
| 2010/0286351 | A1 | 11/2010 | Yoshida et al. |
| 2010/0305230 | A1 | 12/2010 | Li et al. |
| 2011/0186544 | A1 | 8/2011 | Endou et al. |
| 2011/0253946 | A1 | 10/2011 | Huh et al. |
| 2011/0294070 | A1 | 12/2011 | Hatakeyama et al. |
| 2012/0052446 | A1 | 3/2012 | Jaycox et al. |
| 2012/0116024 | A1 | 5/2012 | Iyoda et al. |
| 2012/0214094 | A1 | 8/2012 | Mikoshiba et al. |
| 2013/0048488 | A1 | 2/2013 | Shufflebotham |
| 2013/0078576 | A1 | 3/2013 | Wu et al. |
| 2013/0183828 | A1 | 7/2013 | Nakamura et al. |
| 2013/0189504 | A1 | 7/2013 | Nealey et al. |
| 2013/0209693 | A1 | 8/2013 | Vogel et al. |
| 2013/0209755 | A1 | 8/2013 | Hustad et al. |
| 2013/0248488 | A1 | 9/2013 | Han et al. |
| 2013/0284698 | A1 | 10/2013 | Ogihara |
| 2013/0306594 | A1 | 11/2013 | Hustad et al. |
| 2014/0011916 | A1 | 1/2014 | Lee et al. |
| 2014/0127456 | A1 | 5/2014 | Regner |
| 2014/0141375 | A1 | 5/2014 | Cho et al. |
| 2014/0238954 | A1 | 8/2014 | Matsumiya et al. |
| 2014/0370442 | A1 | 12/2014 | Ober et al. |
| 2015/0064630 | A1 | 3/2015 | Wuister et al. |
| 2015/0085042 | A1 | 3/2015 | Keoshkerian et al. |
| 2015/0197663 | A1 | 7/2015 | Mizutani et al. |
| 2015/0228298 | A1 | 8/2015 | Han et al. |
| 2016/0204653 | A1 | 7/2016 | Lee |
| 2016/0257838 | A1 | 9/2016 | Senzaki et al. |
| 2016/0280823 | A1 | 9/2016 | Kim et al. |
| 2016/0280831 | A1 | 9/2016 | Park et al. |
| 2016/0280832 | A1 | 9/2016 | Kim et al. |
| 2016/0280833 | A1 | 9/2016 | Lee et al. |
| 2016/0280834 | A1 | 9/2016 | Kim et al. |
| 2016/0280835 | A1 | 9/2016 | Lee et al. |
| 2016/0304653 | A1 | 10/2016 | Kim et al. |
| 2016/0304654 | A1 | 10/2016 | Lee et al. |
| 2016/0304655 | A1 | 10/2016 | Lee et al. |
| 2016/0311958 | A1 | 10/2016 | Kim et al. |
| 2016/0311959 | A1 | 10/2016 | Lee et al. |
| 2016/0311960 | A1 | 10/2016 | Lee et al. |

(56) References Cited

U.S. PATENT DOCUMENTS

| | | |
|---|---|---|
| 2016/0333221 A1 | 11/2016 | Mumtaz et al. |
| 2017/0008992 A1 | 1/2017 | Lee et al. |
| 2017/0058071 A1 | 3/2017 | Lee et al. |
| 2017/0210938 A1 | 7/2017 | Ku et al. |
| 2017/0219922 A1 | 8/2017 | Ku et al. |
| 2017/0226235 A1 | 8/2017 | Park et al. |
| 2017/0226258 A1 | 8/2017 | Lee et al. |
| 2017/0226260 A1 | 8/2017 | Lee et al. |
| 2017/0226261 A1 | 8/2017 | Lee et al. |
| 2017/0247492 A1 | 8/2017 | Choi et al. |
| 2017/0306074 A1 | 10/2017 | Lee et al. |
| 2017/0313869 A1 | 11/2017 | Lee et al. |
| 2018/0170023 A1 | 6/2018 | Park et al. |

FOREIGN PATENT DOCUMENTS

| | | |
|---|---|---|
| CN | 101215362 A | 7/2008 |
| CN | 101443371 A | 5/2009 |
| CN | 101492520 A | 7/2009 |
| CN | 101578232 A | 11/2009 |
| CN | 101688047 A | 3/2010 |
| CN | 101799626 A | 8/2010 |
| CN | 101977839 A | 2/2011 |
| CN | 102172491 A | 9/2011 |
| CN | 102439076 A | 5/2012 |
| CN | 102967918 A | 3/2013 |
| CN | 103025827 A | 4/2013 |
| CN | 103180783 A | 6/2013 |
| CN | 103289285 A | 9/2013 |
| CN | 103562245 A | 2/2014 |
| CN | 103797066 A | 5/2014 |
| CN | 105899556 A | 8/2016 |
| CN | 105899557 A | 8/2016 |
| CN | 105899559 A | 8/2016 |
| CN | 105899560 A | 8/2016 |
| CN | 105934454 A | 9/2016 |
| CN | 105934456 A | 9/2016 |
| CN | 105960422 A | 9/2016 |
| CN | 105980342 A | 9/2016 |
| CN | 106459326 A | 2/2017 |
| CN | 107075052 A | 8/2017 |
| EP | 1141056 B1 | 8/2010 |
| EP | 2781550 A1 | 9/2014 |
| EP | 3078654 A1 | 10/2016 |
| EP | 3078691 B1 | 10/2016 |
| EP | 3078692 A1 | 10/2016 |
| EP | 3078694 A1 | 10/2016 |
| EP | 3203497 A1 | 8/2017 |
| EP | 3214102 A1 | 9/2017 |
| EP | 3225641 A1 | 10/2017 |
| GB | 898065 A | 6/1962 |
| JP | 01260360 A | 10/1989 |
| JP | H01260360 A | 10/1989 |
| JP | H5320281 A | 12/1993 |
| JP | H0665333 A | 3/1994 |
| JP | H0245427 A | 9/1998 |
| JP | H10237143 A | 9/1998 |
| JP | H1143523 A | 2/1999 |
| JP | 2000053734 A | 2/2000 |
| JP | 2000281737 A | 10/2000 |
| JP | 2000285751 A | 10/2000 |
| JP | 3121116 B2 | 12/2000 |
| JP | 2001513125 A | 8/2001 |
| JP | 2001294617 A | 10/2001 |
| JP | 2002145973 A | 5/2002 |
| JP | 2003536105 A | 12/2003 |
| JP | 2004026688 A | 1/2004 |
| JP | 2004323773 A | 11/2004 |
| JP | 2005015508 A | 1/2005 |
| JP | 2005097442 A | 4/2005 |
| JP | 2005148205 A | 6/2005 |
| JP | 2005530030 A | 10/2005 |
| JP | 2005531618 A | 10/2005 |
| JP | 2007070453 A | 3/2007 |
| JP | 2007077292 A | 3/2007 |
| JP | 2007246600 A | 9/2007 |
| JP | 200855579 A | 3/2008 |
| JP | 2009057519 A | 3/2009 |
| JP | 200986354 A | 4/2009 |
| JP | 2009203439 A | 9/2009 |
| JP | 2010507803 A | 3/2010 |
| JP | 2010115832 A | 5/2010 |
| JP | 2010116466 A | 5/2010 |
| JP | 2010145158 A | 7/2010 |
| JP | 2010202723 A | 9/2010 |
| JP | 2010275349 A | 12/2010 |
| JP | 4625901 B2 | 2/2011 |
| JP | 2012001787 A | 1/2012 |
| JP | 2012012577 A | 1/2012 |
| JP | 2012036078 A | 2/2012 |
| JP | 2012093699 A | 5/2012 |
| JP | 2012174984 A | 9/2012 |
| JP | 201368882 A | 4/2013 |
| JP | 2013512323 A | 4/2013 |
| JP | 2013514449 A | 4/2013 |
| JP | 2013121430 A | 6/2013 |
| JP | 2013219334 A | 10/2013 |
| JP | 2013232501 A | 11/2013 |
| JP | 201412807 A | 1/2014 |
| JP | 2014070154 A | 4/2014 |
| JP | 2014078014 A | 5/2014 |
| JP | 2014102503 A | 6/2014 |
| JP | 2014160770 | 9/2014 |
| JP | 2014162504 A | 9/2014 |
| JP | 2015000896 A | 1/2015 |
| JP | 2016539239 A | 12/2016 |
| JP | 2016540863 A | 12/2016 |
| JP | 2017502116 A | 1/2017 |
| JP | 2017505356 A | 2/2017 |
| JP | 2017530236 A | 10/2017 |
| JP | 2017530238 A | 10/2017 |
| JP | 2017533302 A | 11/2017 |
| KR | 20010101356 | 11/2001 |
| KR | 100622353 B1 | 9/2006 |
| KR | 20090015742 A | 2/2009 |
| KR | 100935863 B1 | 1/2010 |
| KR | 20100033962 A | 3/2010 |
| KR | 20100070380 A | 6/2010 |
| KR | 20100123920 A | 11/2010 |
| KR | 20110018678 A | 2/2011 |
| KR | 20110086834 A | 8/2011 |
| KR | 20110097707 A | 8/2011 |
| KR | 20110102998 A | 9/2011 |
| KR | 20110112501 A | 10/2011 |
| KR | 101102680 B1 | 1/2012 |
| KR | 20120119998 A | 11/2012 |
| KR | 20130094264 A | 8/2013 |
| KR | 20130113596 A | 10/2013 |
| KR | 20130128346 A | 11/2013 |
| KR | 20140063790 A | 5/2014 |
| KR | 20150066488 A | 6/2015 |
| KR | 20150067065 A | 6/2015 |
| KR | 20150067069 A | 6/2015 |
| KR | 20150067070 A | 6/2015 |
| KR | 20160038705 A | 4/2016 |
| TW | 201323461 A | 6/2013 |
| TW | 201428046 A | 7/2014 |
| TW | 201536823 A | 10/2015 |
| TW | 201538548 A | 10/2015 |
| WO | 9837136 A1 | 8/1998 |
| WO | 2007055371 A1 | 5/2007 |
| WO | 2012144735 A2 | 10/2012 |
| WO | 2013069544 A1 | 5/2013 |
| WO | 2013120051 A1 | 8/2013 |
| WO | 2013158527 A1 | 10/2013 |
| WO | 2014050905 A1 | 4/2014 |
| WO | 2014090178 A1 | 6/2014 |
| WO | 2014124795 A1 | 8/2014 |
| WO | 2015084121 A1 | 6/2015 |
| WO | 2015084122 A1 | 6/2015 |
| WO | 2015084123 A1 | 6/2015 |
| WO | 2015084124 A1 | 6/2015 |
| WO | 2015084125 A1 | 6/2015 |
| WO | 2015084126 A1 | 6/2015 |

(56) References Cited

FOREIGN PATENT DOCUMENTS

| WO | 2015084127 A1 | 6/2015 |
|---|---|---|
| WO | 2015084129 A1 | 6/2015 |
| WO | 2015087005 A1 | 6/2015 |
| WO | 2016052994 A1 | 4/2016 |
| WO | 2016052999 A1 | 4/2016 |
| WO | 2016053005 A1 | 4/2016 |
| WO | 2016053007 A1 | 4/2016 |
| WO | 2016053011 A1 | 4/2016 |

OTHER PUBLICATIONS

Chinese Search Report for Application No. 2014800741401 dated Mar. 9, 2018.
Chinese Search Report for Application No. 2014800727599 dated Jan. 8, 2018.
Beng H. Tan et al., "Synthesis and Self-Assembly of pH-Responsive Amphiphilic Poly (dimethylaminoethylmethacrylate)-block-Poly(pentafluorostyrene) Block Copolymer in Aqueous Solution", Macromolecular Rapid Communications, 2009, vol. 30, pp. 1002-1008.
Chinese Search Report for CN Application No. 201480074044.7 dated Jun. 7, 2018.
Frank S. Bates et al., "Block Copolymer Thermodyanmics: Theory and Experiment", Annu. Rev. Phys. Chem., 1990, vol. 41, pp. 525-557.
G.R. Strobl, "The Physics of Polymers: Concepts for Understanding Their Structures and Behavior", Springer (Abstract Only).
S. Chavda et al., "Synthesis of stimuli responsive PEG47-b-PAA126-b-PSt32 triblock copolymer and its self-assembly in aqueous solutions", European Polymer Journal, Sep. 2012, vol. 49, pp. 209-216.
Sachin Borkar et al., "New Highly Fluorinated Styrene-Based Materials with Low Surface Energy Prepared by ATRP", Macromolecules, Jan. 2004, vol. 37, pp. 788-794.
U.S. Appl. No. 15/102,139, filed Jun. 6, 2016.
U.S. Appl. No. 15/102,149, filed Jun. 6, 2016.
U.S. Appl. No. 15/102,156, filed Jun. 6, 2016.
U.S. Appl. No. 15/173,670, filed Jun. 5, 2016.
U.S. Appl. No. 15/173,671, filed Jun. 5, 2016.
U.S. Appl. No. 15/173,673, filed Jun. 5, 2016.
U.S. Appl. No. 15/173,674, filed Jun. 5, 2016.
U.S. Appl. No. 15/173,676, filed Jun. 5, 2016.
U.S. Appl. No. 15/514,929, filed Mar. 28, 2017.
U.S. Appl. No. 15/514,939, filed Mar. 28, 2017.
U.S. Appl. No. 15/514,959, filed Mar. 28, 2017.
U.S. Appl. No. 15/514,967, filed Mar. 28, 2017.
U.S. Appl. No. 15/515,293, filed Mar. 29, 2017.
U.S. Appl. No. 15/515,432, filed Mar. 29, 2017.
U.S. Appl. No. 15/515,812, filed Mar. 30, 2017.
U.S. Appl. No. 15/515,818, filed Mar. 30, 2017.
U.S. Appl. No. 15/515,821, filed Mar. 30, 2017.
CN Search Report for Application No. 201480071920.0 dated Aug. 2, 2017.
CN Search Report for Application No. CN201480072884.X dated Aug. 3, 2017.
CN Search Report for Application No. CN2014800740447 dated Aug. 1, 2017.
Extended European Search Report for Application No. EP14867273 dated Aug. 10, 2017.
Mariana Beija et al: "Fluorescence Anisotropy of Hydrophobic Probes in poly(N-decylacrylamide) block-poly(N, N-diethylacrylamide) Block Copolymer Aqueous Solutions: Evidence of Premicellar Aggregates" Journal of Physical Chemistry Part B: Condensed Matter, Materials, Surfaces, Interfaces & BiOphysical, vol. 114, No. 31, Aug. 12, 2010 (Aug. 12, 2010), 9977-9986, XP055394763, US ISSN: 1520-6106, DOI: 10.1021/jp101613y * abstract * * Scheme 1, PDcA11-block-PDEA295; p. 9978 *.
Chakrabarty, et al., "Tailor-Made Polyfluoroacrylate and its Block Copolymer by RAFT Polymerization in Miniemulsion; Improved Hydrophobicity in the Core-Shell Block Copolymer", Journal of Colloid and Interface Science, vol. 408, Oct. 2013, pp. 66-74.
Gregory, et al., "Complex Polymer Architectures via RAFT Polymerization: From Fundamental Process to Extending the Scope Using Click Chemistry and Nature's Building Blocks", Progress in Polymer Science, vol. 37, No. 1, Jan. 2012, pp. 38-105.
Akiba, Isamu, et al., "Self-Assembly of Amphiphilic Block Copolymers Containing Poly(n-octadecyl acrylate) Block in Aqueous Solution." IOP Conference Series: Materials Science and Engineering, 2010, vol. 14, No. 1, pp. 1-8.
Hua et al. Temperature-induced phase-transitions of methoxyoligo(oxyethylene) styrene-based block copolymers in aqueous solution, Soft Matter, 2013, 9, 8897.
International Search Report from PCT/KR2014/012023, dated Mar. 10, 2015.
International Search Report from PCT/KR2014/012024, dated Mar. 17, 2015.
International Search Report from PCT/KR2014/012025, dated Mar. 17, 2015.
International Search Report from PCT/KR2014/012026, dated Mar. 17, 2015.
International Search Report from PCT/KR2014/012027, dated Mar. 17, 2015.
International Search Report from PCT/KR2014/012028, dated Mar. 17, 2015.
International Search Report from PCT/KR2014/012029, dated Mar. 17, 2015.
International Search Report from PCT/KR2014/012030, dated Mar. 17, 2015.
International Search Report from PCT/KR2014/012031, dated Feb. 12, 2015.
International Search Report from PCT/KR2014/012032, dated Feb. 12, 2015.
International Search Report from PCT/KR2014/012033, dated Feb. 12, 2015.
International Search Report from PCT/KR2014/012034, dated Feb. 12, 2015.
International Search Report from PCT/KR2014/012035, dated Feb. 12, 2015.
International Search Report from PCT/KR2014/012036, dated Mar. 17, 2015.
International Search Report from PCT/KR2015/010313, dated Nov. 23, 2015.
International Search Report from PCT/KR2015/010320, dated Jan. 13, 2016.
International Search Report from PCT/KR2015/010322, dated Jan. 13, 2016.
International Search Report from PCT/KR2015/010323, dated Jan. 13, 2016.
International Search Report from PCT/KR2015/010327, dated Jan. 12, 2016.
International Search Report from PCT/KR2015/010330 dated Jan. 11, 2016.
International Search Report from PCT/KR2015/010332 dated Jan. 13, 2016.
International Search Report from PCT/KR2015/010334, dated Jan. 13, 2016.
International Search Report from PCT/KR2015/010335 dated Jan. 13, 2016.
International Search Report from PCT/KR2015/010338 dated Jan. 14, 2016.
IPO Search Report from Taiwan Application No. 103142745, dated Dec. 14, 2015.
IPO Search Report from Taiwan Application No. 103142777, dated Dec. 15, 2015.
IPO Search Report from Taiwan Application No. 103142780, dated Dec. 15, 2015.
IPO Search Report from Taiwan Application No. 103142784, dated Jan. 27, 2016.
IPO Search Report from Taiwan Application No. 103142786, dated Jan. 11, 2016.
IPO Search Report from Taiwan Application No. 103142790, dated Dec. 15, 2015.

(56) References Cited

OTHER PUBLICATIONS

IPO Search Report from Taiwan Application No. 103142794, dated Dec. 15, 2015.
IPO Search Report from Taiwan Application No. 103142798, dated Dec. 16, 2015.
IPO Search Report from Taiwan Application No. 103142805, dated Dec. 11, 2015.
IPO Search Report from Taiwan Application No. 103142955, dated Jan. 15, 2016.
IPO Search Report from Taiwan Application No. 103142956 dated Jan. 20, 2016.
IPO Search Report from Taiwan Application No. 103142963, dated Dec. 10, 2015.
IPO Search Report from Taiwan Application No. 104132186, dated Aug. 18, 2016.
IPO Search Report from Tawain Application No. 103142782, dated Dec. 11, 2015.
Khazimullis et al. "Gel formation in a mixture of a block copolymer and a nematic liquid crystal", Physical Review E 84, 021710 (2011).
Park et al., "Block Copolymer Lithography: Periodic Arrays of ~10 11 Holes in 1 Square Centimeter", Science 276, pp. 1401-1404, May 30, 1997.
Tenneti et al. "Competition between liquid crystallinity and block copolymer self-assembly in core-shell rod-coil block ,copolymers", Soft Matter, 2008, 4, 458-461 (2008).
Tenneti et al. Hierarchical Nanostructures of Mesogen Jacketed Bent-Core Liquid Crystalline Block Copolymers, Proceedings Published 2007 by the American Chemical Society.
U.S. Appl. No. 15/101,794, filed Jun. 3, 2016.
U.S. Appl. No. 15/101,812, filed Jun. 3, 2016.
U.S. Appl. No. 15/101,827, filed Jun. 3, 2016.
U.S. Appl. No. 15/101,915, filed Jun. 5, 2016.
U.S. Appl. No. 15/102,089, filed Jun. 6, 2016.
U.S. Appl. No. 15/102,112, filed Jun. 6, 2016.
EESR for EP Application No. 15847536.8 dated Aug. 23, 2018, 6 pages.
Database CA [Online] Chemical Abstracts Service Ohi0 US; Zou, Yue: "Fluorosurfactant capable of preventing unevenness in photoresist coating and its preparation by anionic polymerization", XP002771143 retrieved from STN Database accession No. 2011:1148166 * abstract * & CN 102 172 491 A (Jiangsu Johnny Material Technology Co Ltd) Sep. 7 011 (Sep. 7, 2011) Columbus, No. 2011:1148166.
European Search Report for Application No. EP14867501 dated Jul. 14, 2017.
Kago K et al: "X-ray reflectivity of polymer assembly at air-water interface" Supramolecular Science Butterworth-Heinemann Oxford GB vol. 5 No. 3-4, Jul. 1, 1998 (Jul. 1, 1998)pp. 349-355 XP027388373 ISSN: 0968-5677 [retrieved on Jul. 1, 1998] * abstract *.
Lutz Funk et al: "Novel Amphiphilic Styrene-Based Block Copolymers for Induced Surface Reconstruction". Macromolecular Chemistry and Physics., vol. 209, No. 1, Jan. 4, 2008 (Jan. 4, 2008), XP055382259 DE ISSN: 1022-1352 D0I: 10.1002/macp. 200700312 * scheme 1, monomers M1, M4 table 2*.
Mori H et al: "Synthesis and Surface Characterization of Hydrophilic-Hydrophobic Block Copolymers Containing Poly(2, 3-Dihydroxypropyl Methacrylate) " Macromolecules American Chemical Society US vol. 27 No. 15 Jul. 18, 1994 (Jul. 18, 1994) pp. 4093-4100 XP000456650 ISSN: 0024-9297 D01: 10.1021/MA00093A010 * abstract *.
Chinese Search Report for Application No. 201480074156.2 dated Apr. 3, 2018.
Supplementary European Search Report for EP15847157 dated Mar. 21, 2018.
Anonymous., "Solid surface energy data (SFE) for common polymers", surface-tension.de, Feb. 2017, Retreived from the Internet: URL:http://www.surface-tension.de/solid-surface-energy.htm, XP002775246.
Cummins et al., "Solvothermal Vapor Annealing of Lamellar Poly-(styrene)-block-poly(D,L-lactide) Block Copolymer Thin Films for Directed Self-Assembly Application", ACS Applied Materials & Interfaces, Mar. 2016, vol. 8, No. 12, pp. 8295-8304, XP055419698.
Extended European Search Report for Application No. EP14867808.9 dated Nov. 10, 2017.
Extended European Search Report for Application No. EP14868022.6 dated Nov. 6, 2017.
Extended European Search Report for Application No. EP14868320.4 dated Nov. 20, 2017.
Extended European Search Report for Application No. EP14868480.6 dated Nov. 2, 2017.
Hvilsted et al., "Novel Fluorinated Polymer Materials Based on 2,3,5,6-Tetrafluoro-4-methoxyystyrene" In: "Advances in Controlled/Living Radical Polymerization", American Chemical Society, Jun. 26, 2003, vol. 854, pp. 236-249, XP055421064.
Mahajan et al., "Synthesis and Characterization of Amphiphilic Poly(ethylene oxide)-block-poly(hexylmethacrylate Copolymers", Macromolecular Chemistry and Physics, Wiley-Vch Verlag, Weinheim, DE, Jan. 2003, vol. 204, pp. 1047-1055, XP003030406.
Pochan et al., "Morphologies of microphase-seperated conformationally asymmetric diblock copolymers", Journal of Polymer Science Part B: Polymer Physics, Nov. 2017, vol. 35, No. 16, pp. 2629-2643, XP055417266.
Zhuang et al., "Synthesis of A-B type block copolymers using 1-phenylethyl dithiobenzoate as Reversible Addition-Fragmentation Chain Transfer agent", Database CA [online], Chemical Abstracts Service, Columbus, OH, XP002775247.
Chinese Search Report for Application No. 201480072759.9 dated Jan. 24, 2018.
Chinese Search Report for CN Application No. 201480071920.0, dated May 4, 2018.
Chinese Search Report for CN Application No. 201480072800.2, dated Apr. 10, 2018.
Chinese Search Report for CN Application No. 201480074045.1, dated Apr. 11, 2018.
Extended European Seach Report including Written Opinion for EP Application No. 15847574.9, dated May 3, 2018.
Extended European Search Report including Written Opinion for EP Application No. 15845928.9, dated May 2, 2018.
Extended European Search Report including Written Opinion for EP Application No. 15847598.8, dated May 11, 2018.
Extended European Search Report including Written Opinion for EP15845720.0 dated May 4, 2018.
Extended European Search Report with Written Opinion for EP158468322 dated May 3, 2018.
Funk, L. et al., "Novel Amphiphilic Styrene-Based Block Copolymers for Induced Surface Reconstruction," Macromolecular Chemistry and Physics, vol. 209, No. 1, Jan. 4, 2008, pp. 52-63, XP055382259, DE, ISSN: 1022-1352, DOI: 10.1002/macp. 200700312.
Haeng-Dong Koh et al., "Location-controlled parallel and vertical orientation by dewetting-induced block copolymer directed self-assembly," Journal of Materials Chemistry C: Materials for Optical and Electronic Devices, vol. 1, No. 25, Jan. 1, 2013, pp. 4020-4024 XP055469744.
Ma J et al., "Synthesis and Solution-State Assembly or Buld State Thiol-ene Crosslinking of Pyrrolidinone- and Alkene-Functionalized Amphiphilic Block Fluorocopoplymers: From Functional Nanoparticles to Anti-Fouling Coatings", Australian Journal of Chemistry: An International Journal for Chemical Sci, Jan. 1, 2010, pp. 1159-1163, vol. 63, No. 8,C S I R O Publishing, Australia.
Mori H. et al., "Synthesis and Surface Characterization of Hydrophilic-Hydrophobic Block Copolymers Containing Poly(2,3-dihydroxypropyl methacrylate)," Macromolecules, American Chemical Society, US, vol. 27, No. 15, Jul. 18, 1994, pp. 4093-9297; XP000456650, DOI: 10.2021/MA00093A010.
Segalman R.A. et al., "Graphoepitaxy of Spherical Domain Block Copolymer Films," Advanced Materials, Wiley-VCH Verlag GmbH & Co. KGAA, DE, vol. 13, No. 15, Aug. 3, 2001, pp. 1152-1155; XP001129643, ISSN: 0935-9648, DOI: 10.1002/1521-4095(200108)13:15<1152: AID-A DMA1152>3.0.CO; 2-5.

(56) References Cited

OTHER PUBLICATIONS

C.M. Bates et al., "Polymeric Cross-Linked Surface Treatments for Controlling Block Copolymer Orientation in Thin Films", Langmuir Article, American Chemical Society, Jan. 7, 2011, vol. 27, No. 5, pp. 1-7.
Extended European Search Report including Written Opinion for Application No. EP15845665.7 dated Jun. 27, 2018.
Katja Nilles et al., "RAFT Polymerization of Activated 4-Vinylbenzoates"., Journal of Polymer Science: Part A: Polymer Chemistry, Jan. 1, 2009, vol. 47, pp. 1696-1705.
Truelsen et al., "Synthesis by ATRP of triblock copolymers with densely grafted styrenic end blocks from a polyisobutylene macroinitiator", Marcomol. Rapid. Commun., Jul. 2, 1999, vol. 21, No. 2, pp. 1-5.
Palacios et al., Constructing Robust and Functional Micropatterns on Polystyrene Surfaces by Using Deep UV Irradiation, American Chemical Society, Langmuir, 29(8) pp. 2756-2763, Feb. 2013.
Riedel et al., Synthesis, post-modification and self-assembled thin films of pentafluorostyrene containing block copolymers, European Polymer Journal 47 (2011) 675-684.
Yoshida, E. et al. Polymer Journal vol. 31 (5) pp. 429-434 (1999).
Chinese Search Report for Application No. CN201580059758.5 dated Sep. 5, 2018.
Chinese Search Report for Application No. CN201580060097.8 dated Sep. 19, 2018.
CN Search Report for Application No. CN201580059710.4. dated Sep. 3, 2018.
Extended European Search Report including Written Opinion for EP Application 15846126.9 dated Sep. 12, 2018.
Naoko Kihara., "Self-Organizing Lithography Technology", Toshiba Review, Apr. 1, 2012, vol. 67, No. 4, pp. 44-47 (Abstract Only).

\* cited by examiner

BLOCK COPOLYMER

CROSS-REFERENCE TO RELATED APPLICATIONS

The present application is a national phase entry under 35 U.S.C. § 371 of International Application No. PCT/KR2015/010323, filed Sep. 30, 2015, published in Korean, which claims priority to and the benefit of Korean Patent Application No. 2014-0131964, filed on Sep. 30, 2014, and No. 2015-0079480, filed on Jun. 4, 2015, the disclosures of which are incorporated herein by reference in their entirety.

FIELD

The present application relates to a block copolymer and uses thereof.

BACKGROUND

The block copolymer has a molecular structure in which polymer blocks having different chemical structures from one another are connected to one another by covalent bonds. The block copolymer can form a regularly arranged structure, such as a sphere, a cylinder and a lamella, by phase separation. The size of a domain that is formed by the self-assembly phenomenon of a block copolymer can be adjusted over a wide range, and the domain can be produced into various structures which can be applied to the production of a variety of next-generation nanodevices, magnetic storage media, and patterns (by lithography or the like), for example, the formation of high-density magnetic recording media, nanowires, quantum dots, or metal dots.

DESCRIPTION

Object

The present application provides block copolymers and uses thereof.

Solution

Unless specifically indicated otherwise, the term "an alkyl group" in the present specification may refer to an alkyl group with 1 to 20 carbons, 1 to 16 carbons, 1 to 12 carbons, 1 to 8 carbons or 1 to 4 carbons. The above alkyl group may be a linear-type, a branched-type or a ring-type, and it may be optionally substituted in part by one or more substituents.

Unless specifically indicated otherwise, the term "an alkoxy group" in the present specification may refer to an alkoxy group with 1 to 20 carbons, 1 to 16 carbons, 1 to 12 carbons, 1 to 8 carbons or 1 to 4 carbons. The above alkoxy group may be a linear-type, a branched-type or a ring-type, and it may be optionally substituted in part by one or more substituents.

Unless specifically indicated otherwise, the term "an alkenyl group" or "an alkynyl group" in the present specification may refer to an alkenyl group or alkynyl group with 2 to 20 carbons, 2 to 16 carbons, 2 to 12 carbons, 2 to 8 carbons or 2 to 4 carbons. The above alkenyl group or alkynyl group may be a linear-type, a branched-type or a ring-type, and it may be optionally substituted in part by one or more substituents.

Unless specifically indicated otherwise, the term "an alkylene group" in the present specification may refer to an alkylene group with 1 to 20 carbons, 1 to 16 carbons, 1 to 12 carbons, 1 to 8 carbons or 1 to 4 carbons. The above alkylene group may be a linear-type, a branched-type or a ring-type, and it may be optionally substituted in part by one or more substituents.

Unless specifically indicated otherwise, the terms "an alkenylene group" or "an alkynylene group" in the present specification may refer to an alkenylene group or alkynylene group with 2 to 20 carbons, 2 to 16 carbons, 2 to 12 carbons, 2 to 8 carbons or 2 to 4 carbons. The above alkenylene group or alkynylene group may be a linear-type, a branched-type or a ring-type, and it may be optionally substituted in part by one or more substituents.

Unless specifically indicated otherwise, the term "an aryl group" or "an arylene group" in the present specification may refer to a monovalent or divalent residue that is derived from a compound that has a benzene ring structure or a structure in which two or more benzene rings are connected to one another (either by sharing one or two carbon atoms or by any linker) or from a derivative of the above compound. Unless specifically indicated otherwise, the above aryl group or arylene group may refer to an aryl group with, for example, 6 to 30 carbons, 6 to 25 carbons, 6 to 21 carbons, 6 to 18 carbons, or 6 to 13 carbons.

In the present application, the term "an aromatic structure" may refer to the above aryl group or arylene group.

In the present specification, the term "an alicyclic ring structure" refers to, unless specifically indicated otherwise, a ring-type hydrocarbon atom structure other than an aromatic ring structure. Unless specifically indicated otherwise, the above alicyclic ring structure may refer to an alicyclic ring structure with, for example, 3 to 30 carbons, 3 to 25 carbons, 3 to 21 carbons, 3 to 18 carbons, or 3 to 13 carbons.

In the present application, the term "a single bond" may refer to the case in which a particular atom is not present in the corresponding area. For example, when B denotes a single bond in the structure that is represented by A-B-C, it may be assumed that there is no particular atom present in the region that is marked as B, resulting in a direct connection between A and C to form the structure that is represented by A-C.

In the present application, examples of the substituent that may be optionally substituted for a part or parts of an alkyl group, an alkenyl group, an alkynyl group, an alkylene group, an alkenylene group, an alkynylene group, an alkoxy group, an aryl group, an arylene group, a chain, an aromatic structure or the like may include, but are not limited to, a hydroxyl group, a halogen atom, a carboxyl group, a glycidyl group, an acryloyl group, a methacryloyl group, an acryloyloxy group, a methacryloyloxy group, a thiol group, an alkyl group, an alkenyl group, an alkynyl group, an alkylene group, an alkenylene group, an alkynylene group, an alkoxy group, and an aryl group.

A block copolymer of the present application may contain a block that is a structural unit represented by the following Structural Formula 1.

[Structural Formula 1]

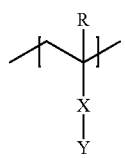

In Structural Formula 1, R represents a hydrogen atom or an alkyl group; X represents a single bond, an oxygen atom, a sulfur atom, —NR$_1$—, —S(=O)$_2$—, a carbonyl group, an alkylene group, an alkenylene group, an alkynylene group, —C(=O)—X$_1$— or —X$_1$—C(=O)—, where the X$_1$ represents a single bond, an oxygen atom, a sulfur atom, —NR$_1$—, —S(=O)$_2$—, an alkylene group, an alkenylene group or an alkynylene group, where the R$_1$ represents a hydrogen atom or an alkyl group; and Y represents an aryl group substituted in at least one part by a substituent (that is represented by -Q-P), where the Q represents —K—C(=O)—X$_2$—, —X$_2$—C(=O)—K— or a cycloalkylene group, where the X$_2$ represents an oxygen atom, a sulfur atom, —S(=O)$_2$—, an alkylene group, an alkenylene group or an alkynylene group and the K represents an alkenylene group, and the P represents a chain including 3 or more chain-forming atoms.

In another example, the X of Structural Formula 1 may represent a single bond, an oxygen atom, a carbonyl group, —C(=O)—O—, —O—C(=O)—, or —C(=O)—O—.

In Structural Formula 1, Y represents an aryl group that is substituted in at least one part by a substituent (that is represented by -Q-P), and it may be, for example, an aryl group (with 6 to 18 carbons or 6 to 12 carbons) or a phenyl group. The aryl group may be substituted in one or more parts, for example, in 1 to 3 parts or 1 to 2 parts, by the above substituent that is represented by -Q-P. When the aryl group is substituted in one part by the above substituent and refers to a phenyl group, the substituent may be substituted in the para position of the phenyl group with respect to X in Structural Formula 1. The aryl group may also be substituted in part by one or more of the other aforementioned substituents in addition to the above substituent as necessary. In addition, the part that is represented by Q in the above substituent may be connected to the aryl group to substitute for a part of the aryl group.

In another example, the Q of the above substituent may be —K—C(=O)—O—, —O—C(=O)—K— or an cycloalkylene group, where the K may be an alkenylene group with 2 to 20 carbons, 2 to 16 carbons, 2 to 12 carbons, 2 to 8 carbons, or 2 to 4 carbons. In addition, the cycloalkylene group may be a cycloalkylene with 3 to 12 carbons.

The P of the above substituent represents a chain structure constructed by 3 or more chain-forming atoms. In the present application, the term "a chain-forming atom" refers to an atom that forms a linear structure of a predetermined chain. The chain may be a linear-type or a branched-type, but the number of chain-forming atoms is counted only by the number of atoms that form the longest linear chain, and the other atoms that are bonded to the above chain-forming atoms (e.g. when the chain-forming atom is a carbon atom, the hydrogen atom or the like that is bonded to the carbon atom) are not taken into account. In the case of a branched-type chain, the number of chain-forming atoms may be counted by the number of chain-forming atoms that form the longest chain. For example, when the chain is an n-pentyl group, all of the chain-forming atoms are carbon and the number of the chain-forming atoms is five, and when the above chain is a 2-methylpentyl group, all of the chain-forming atoms are carbon and the number of the chain-forming atoms is 5. Examples of a chain-forming atom may include carbon, oxygen, sulfur, and nitrogen; a suitable chain-forming atom may be any one of carbon, oxygen and nitrogen, or any one of carbon and oxygen. The number of chain-forming atoms in a chain may be 4 or more, or 5 or more. The number of chain-forming atoms in a chain may also be 30 or less, 25 or less, 20 or less, 16 or less, 12 or less, or 8 or less.

The block containing the structural unit represented by Structural Formula 1 may contain the structural unit represented by Structural Formula 1 either exclusively or together with a suitable amount of other structural unit(s). Such a block may provide an excellent self-assembling property to the block copolymer to which it belongs.

In one example, the aforementioned chain may be a linear hydrocarbon chain such as a linear alkyl group. In such a case, the alkyl group may be an alkyl group with 3 or more carbons, 3 to 30 carbons, 3 to 25 carbons, 3 to 20 carbons, 3 to 16 carbons, 3 to 12 carbons, or 3 to 8 carbons. At least one hydrogen atom in the alkyl group may be optionally substituted by other substituent(s).

There is no particular limitation to the type of the other block (which may be referred to as the block 2 hereinafter) that may be contained in a block copolymer together with the block (which may be referred to as the block 1 hereinafter) that contains the structural unit represented by the Structural Formula 1 above.

Examples of the block 2 may include a polyvinylpyrrolidone block, a polylactic acid block, a poly(vinylpyridine) block, a polystyrene block such as polystyrene and poly(trimethylsilyl styrene), a polyalkylene oxide block such as polyethylene oxide, a polybutadiene block, a polyisoprene block, and a polyolefin block such as polyethylene. In this case, the block may be referred to as a block 2A in the present specification.

In one example, the aforementioned block 2 may be a block that has an aromatic structure with one or more halogen atoms.

The above block 2 may be, for example, the block represented by the following Structural Formula 2. In this case, the block may be referred to as a block 2B in the present specification.

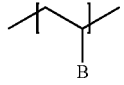

[Structural Formula 2]

In Structural Formula 2, B represents a monovalent substituent that has an aromatic structure with one or more halogen atoms.

Through an excellent interaction with block 1, the above block 2 may provide an excellent self-assembling property to the block copolymer to which it belongs.

The aromatic structure of Structural Formula 2 may be, for example, an aromatic structure with 6 to 18 carbons or 6 to 12 carbons.

In addition, for the halogen atom of Structural Formula 2, a fluorine atom and chlorine atom may be exemplified and a fluorine atom may be preferably selected, although not limited thereto.

In one example, the B of Structural Formula 2 may be a monovalent substituent that has an aromatic structure with 6 to 12 carbons and is substituted in part by 1 or more, 2 or more, 3 or more, 4 or more or 5 or more halogen atoms. There is no particular limitation to the maximum number of the halogen atoms, and there may be, for example, 10 or less, 9 or less, 8 or less, 7 or less or 6 or less halogen atoms present.

For example, the Structural Formula 2 that corresponds to the block 2B may also be represented by the following Structural Formula 3.

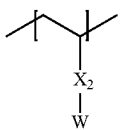
[Structural Formula 3]

In Structural Formula 3, $X_2$ represents a single bond, an oxygen atom, a sulfur atom, —S(=O)$_2$—, an alkylene group, an alkenylene group, an alkynylene group, —C(=O)—$X_1$— or —$X_1$—C(=O)—, where the above $X_1$ represents a single bond, an oxygen atom, a sulfur atom, —S(=O)$_2$—, an alkylene group, an alkenylene group or an alkynylene group; and W represents an aryl group with at least one halogen atom. The W may be an aryl group that is substituted in part by at least one halogen atom; for example, it may be an aryl group with 6 to 12 carbons and is substituted in part by 2 or more, 3 or more, 4 or more or 5 or more halogen atoms.

The block 2B may also be represented, for example, by the following Structural Formula 4.

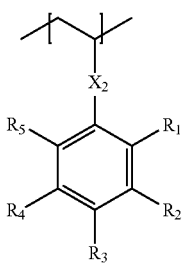
[Structural Formula 4]

In Structural Formula 4, $X_2$ represents a single bond, an oxygen atom, a sulfur atom, —S(=O)$_2$—, an alkylene group, an alkenylene group, an alkynylene group, —C(=O)—$X_1$— or —$X_1$—C(=O)—, where $X_1$ represents a single bond, an oxygen atom, a sulfur atom, —S(=O)$_2$—, an alkylene group, an alkenylene group or an alkynylene group. Each of $R_1$ to $R_5$ independently represents a hydrogen atom, an alkyl group, a haloalkyl group or a halogen atom, and there are one or more halogen atoms in the positions marked as $R_1$ to $R_5$.

In another example, the $X_2$ of Structural Formula 4 may be a single bond, an oxygen atom, an alkylene group, —C(=O)—O—, or —O—C(=O)—.

In Structural Formula 4, each of $R_1$ to $R_5$ independently represents a hydrogen atom, an alkyl group, a haloalkyl group or a halogen atom, and there may be 1 or more, 2 or more, 3 or more, 4 or more or 5 or more halogen atoms (e.g. a fluorine atom) in the positions marked as $R_1$ to $R_5$. The number of the halogen atoms (e.g. a fluorine atom) in the positions marked as $R_1$ to $R_5$ may be 10 or less, 9 or less, 8 or less, 7 or less, or 6 or less.

In one example, the aforementioned block 2 may be the block represented by the following Structural Formula 5. In this case, the block may be referred to as a block 2C in the present specification.

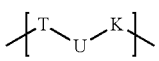
[Structural Formula 5]

In Structural Formula 5, each of T and K independently represents an oxygen atom or a single bond, and U represents an alkylene group.

In one example, the block 2C may be a block that contains an alkylene group with 1 to 20 carbons, 1 to 16 carbons, 1 to 12 carbons, 1 to 8 carbons or 1 to 4 carbons in the position marked as U in the above Structural Formula 5.

The block 2C may be a block in which any one of T and K of the above Structural Formula 5 represents a single bond and the other represents an oxygen atom. In this case, the above U may represent an alkylene group with 1 to 20 carbons, 1 to 16 carbons, 1 to 12 carbons, 1 to 8 carbons, or 1 to 4 carbons.

The above block 2C may also be a block in which both T and K of the above Structural Formula 5 represent an oxygen atom. In this case, the above U may represent an alkylene group with 1 to 20 carbons, 1 to 16 carbons, 1 to 12 carbons, 1 to 8 carbons, or 1 to 4 carbons.

In another example, the aforementioned block 2 may be a block that contains one or more metal atoms or metalloid atoms. In this case, the block may be referred to as a block 2D in the present specification. Such a block may improve, for example, an etching selectivity of a self-assembled film that is formed by using a block copolymer to which the block belongs, during an etching process.

Examples of the metal or metalloid atom(s) that is/are contained in the block 2D may include a silicon atom, an iron atom and a boron atom, but there is no particular limitation to the type, as long as the metal or metalloid atom(s) can result in a suitable etching selectivity of the block copolymer to which it belongs/they belong due to differences from the other atom(s) contained in the same block copolymer.

The block 2D may contain 1 or more, 2 or more, 3 or more, 4 or more or 5 or more halogen atoms (e.g. a fluorine atom) in addition to the above metal or metalloid atom(s). The number of the halogen atoms, such as a fluorine atom, contained in the block 2D may be 10 or less, 9 or less, 8 or less, 7 or less, or 6 or less.

The block 2D may be represented by the following Structural Formula 6.

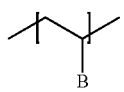
[Structural Formula 6]

In Structural Formula 6, B may represent a substituent with one or more metal atoms or metalloid atoms, or it may be a monovalent substituent that has an aromatic structure with one or more halogen atoms.

The aromatic structure of Structural Formula 6 may be an aromatic structure (e.g. an aryl group or an arylene group) with 6 to 12 carbons.

The second type of the block 2D of Structural Formula 6 may be represented, for example, by the following Structural Formula 7.

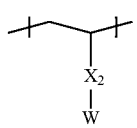
[Structural Formula 7]

In Structural Formula 7, $X_2$ represents a single bond, an oxygen atom, a sulfur atom, $-NR_1-$, $-S(=O)_2-$, an alkylene group, an alkenylene group, an alkynylene group, $-C(=O)-X_1-$ or $-X_1-C(=O)-$, where the $R_1$ represents a hydrogen atom, an alkyl group, an alkenyl group, an alkynyl group, an alkoxy group or an aryl group, where the $X_1$ represents a single bond, an oxygen atom, a sulfur atom, $-NR_2-$, $-S(=O)_2-$, an alkylene group, an alkenylene group or an alkynylene group; and W represents an aryl group that contains a substituent with one or more metal atoms or metalloid atoms and at least one halogen atom.

In the above description, the W may represent an aryl group with 6 to 12 carbons that contains a substituent with one or more metal atoms or metalloid atoms and at least one halogen atom.

In such an aryl group, the number of the substituents with one or more metal atoms or metalloid atoms may be at least one or 1 to 3, and the number of the halogen atoms may be 1 or more, 2 or more, 3 or more, 4 or more, or 5 or more.

In the above description, the number of the halogen atoms may be 10 or less, 9 or less, 8 or less, 7 or less, or 6 or less.

The block 2D of Structural Formula 7 may be represented, for example, by the following Structural Formula 8.

[Structural Formula 8]

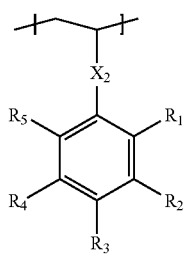

In Structural Formula 8, $X_2$ represents a single bond, an oxygen atom, a sulfur atom, $-NR_1-$, $-S(=O)_2-$, an alkylene group, an alkenylene group, an alkynylene group, $-C(=O)-X_1-$ or $-X_1-C(=O)-$, where the $R_1$ represents a hydrogen atom, an alkyl group, an alkenyl group, an alkynyl group, an alkoxy group or an aryl group, where the $X_1$ represents a single bond, an oxygen atom, a sulfur atom, $-NR_2-$, $-S(=O)_2-$, an alkylene group, an alkenylene group or an alkynylene group; and each of $R_1$ to $R_5$ independently represents a hydrogen atom, an alkyl group, a haloalkyl group, a halogen atom, and a substituent with one or more metal or metalloid atoms, where at least one among $R_1$ to $R_5$ represents a halogen atom, and at least one among $R_1$ to $R_5$ represents a substituent with one or more metal or metalloid atoms.

In Structural Formula 8, at least one, 1 to 3 or 1 to 2 among $R_1$ to $R_5$ may represent the aforementioned substituent with one or more metal atoms or metalloid atoms.

There may be 1 or more, 2 or more, 3 or more, 4 or more or 5 or more halogen atoms in the positions marked as $R_1$ to $R_5$ of Structural Formula 8. Also, the number of halogen atoms in the positions marked as $R_1$ to $R_5$ may be 10 or less, 9 or less, 8 or less, 7 or less or 6 or less.

In the above description, examples of the substituent with one or more metal atoms or metalloid atoms may include a trialkyl siloxy group, a ferrocenyl group, a silsesquioxane group (such as polyhedral oligomeric silsesquioxane), and a carboranyl group, but there is no particular limitation to the type of such a substituent, as long as the substituent can secure an etching selectivity by containing at least one metal or metalloid atom.

In another example, the block 2 may be a block that contains an atom whose electronegativity is 3 or greater and is not a halogen atom (which may be referred to as a nonhalogen atom hereinafter). Such a block may be referred to as a block 2E in the present specification. In another example, the electronegativity of the nonhalogen atom that is contained in the block 2E may be 3.7 or less.

Examples of the nonhalogen atom that is contained in the block 2E may be, but are not limited to, a nitrogen atom and an oxygen atom.

The block 2E may contain 1 or more, 2 or more, 3 or more, 4 or more or 5 or more halogen atoms (e.g. a fluorine atom), in addition to the above nonhalogen atom whose electronegativity is 3 or greater. The number of the halogen atoms, such as a fluorine atom, that are contained in the block 2E may be 10 or less, 9 or less, 8 or less, 7 or less, or 6 or less.

The block 2E may be represented by the following Structural Formula 9.

[Structural Formula 9]

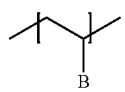

In Structural Formula 9, B may represent a monovalent substituent that has an aromatic structure that contains a substituent (that contains a nonhalogen atom whose electronegativity is 3 or greater) and one or more halogen atoms.

The aromatic structure of Structural Formula 9 may be an aromatic structure (e.g. an aryl group or an arylene group) with 6 to 12 carbons.

In another example, the block of Structural Formula 9 may also be represented by the following Structural Formula 10.

[Structural Formula 10]

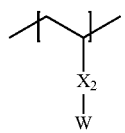

In Structural Formula 10, $X_2$ represents a single bond, an oxygen atom, a sulfur atom, $-NR_1-$, $-S(=O)_2-$, an alkylene group, an alkenylene group, an alkynylene group, $-C(=O)-X_1-$ or $-X_1-C(=O)-$, where the above $R_1$ represents a hydrogen atom, an alkyl group, an alkenyl group, an alkynyl group, an alkoxy group, or an aryl group, and the above $X_1$ represents a single bond, an oxygen atom, a sulfur atom, $-NR_2-$, $-S(=O)_2-$, an alkylene group, an alkenylene group or an alkynylene group; and W represents an aryl group that contains a substituent (that contains a nonhalogen atom whose electronegativity is 3 or greater) and at least one halogen atom.

In the above description, W may be an aryl group with 6 to 12 carbons and contains a substituent (that contains a nonhalogen atom whose electronegativity is 3 or greater) and at least one halogen atom.

In such an aryl group, the number of substituents (each of which contains a nonhalogen atom whose electronegativity is 3 or greater) may be at least one, or 1 to 3. Also, the number of the above halogen atoms may be 1 or more, 2 or more, 3 or more, 4 or more, or 5 or more. In the above description, the number of halogen atoms may also be 10 or less, 9 or less, 8 or less, 7 or less, or 6 or less.

In another example, the block of Structural Formula 10 may be represented by the following Structural Formula 11.

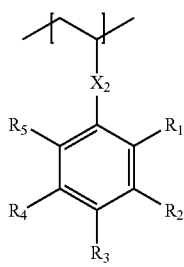

[Structural Formula 11]

In Structural Formula 11, $X_2$ represents a single bond, an oxygen atom, a sulfur atom, $-NR_1-$, $-S(=O)_2-$, an alkylene group, an alkenylene group, an alkynylene group, $-C(=O)-X_1-$, or $-X_1-C(=O)-$, where the above $R_1$ represents a hydrogen atom, an alkyl group, an alkenyl group, an alkynyl group, an alkoxy group, or an aryl group, and the above $X_1$ represents a single bond, an oxygen atom, a sulfur atom, $-NR_2-$, $-S(=O)_2-$, an alkylene group, an alkenylene group, or an alkynylene group, and each of $R_1$ to $R_5$ independently represents a hydrogen atom, an alkyl group, a haloalkyl group, a halogen atom, and a substituent (that contains a nonhalogen atom whose electronegativity is 3 or greater), where at least one among $R_1$ to $R_5$ represents a halogen atom, and at least one among $R_1$ to $R_5$ represents a substituent that contains a nonhalogen atom whose electronegativity is 3 or greater.

In Structural Formula 11, at least one, 1 to 3 or 1 to 2 among $R_1$ to $R_5$ may represent an aforementioned substituent that contains a nonhalogen atom whose electronegativity is 3 or greater.

In Structural Formula 11, there may be 1 or more, 2 or more, 3 or more, 4 or more or 5 or more halogen atoms contained in the positions marked as $R_1$ to $R_5$. Also the number of the halogen atoms contained in the positions marked as $R_1$ to $R_5$ may be 10 or less, 9 or less, 8 or less, 7 or less, or 6 or less.

In the above description, examples of the substituent that contains a nonhalogen atom whose electronegativity is 3 or greater may include, but are not limited to, a hydroxyl group, an alkoxy group, a carboxyl group, an amido group, an ethylene oxide group, a nitrile group, a pyridine group, and an amino group.

In another example, the block 2 may have an aromatic structure that contains a heterocyclic substituent. In this case, the block 2 may be referred to as a block 2F in the present specification.

The block 2F may be represented by the following Structural Formula 12.

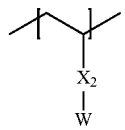

[Structural Formula 12]

In Structural Formula 12, B represents a monovalent substituent having an aromatic structure with 6 to 12 carbons and is substituted by a heterocyclic substituent.

The aromatic structure of Structural Formula 12 may contain, if needed, one or more halogen atoms.

The structural unit of Structural Formula 12 may also be represented by the following Structural Formula 13.

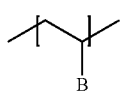

[Structural Formula 13]

In Structural Formula 13, $X_2$ represents a single bond, an oxygen atom, a sulfur atom, $-NR_1-$, $-S(=O)_2-$, an alkylene group, an alkenylene group, an alkynylene group, $-C(=O)-X_1-$ or $-X_1-C(=O)-$, where the $R_1$ represents a hydrogen atom, an alkyl group, an alkenyl group, an alkynyl group, an alkoxy group, or an aryl group, and the $X_1$ represents a single bond, an oxygen atom, a sulfur atom, $-NR_2-$, $-S(=O)_2-$, an alkylene group, an alkenylene group or an alkynylene group; and W represents an aryl group with 6 to 12 carbons and contains a heterocyclic substituent. The structural unit of Structural Formula 13 may also be represented by the following Structural Formula 14.

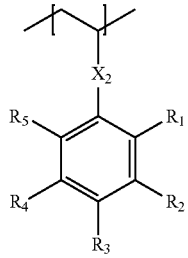

[Structural Formula 14]

In Structural Formula 14, $X_2$ represents a single bond, an oxygen atom, a sulfur atom, $-NR_1-$, $-S(=O)_2-$, an alkylene group, an alkenylene group, an alkynylene group, $-C(=O)-X_1-$ or $-X_1-C(=O)-$, where the $R_1$ represents a hydrogen atom, an alkyl group, an alkenyl group, an alkynyl group, an alkoxy group, or an aryl group, and the $X_1$ represents a single bond, an oxygen atom, a sulfur atom, $-NR_2-$, $-S(=O)_2-$, an alkylene group, an alkenylene group or an alkynylene group; and each of $R_1$ to $R_5$ independently represents a hydrogen atom, an alkyl group, a haloalkyl group, a halogen atom and a heterocyclic substituent, where at least one among $R_1$ to $R_5$ represents a heterocyclic substituent.

In Structural Formula 14, at least one (e.g. 1 to 3 or 1 to 2) among $R_1$ to $R_5$ represents the above heterocyclic substituent, and the rest may represent a hydrogen atom, an alkyl group or a halogen atom; a hydrogen atom or halogen atom; or a hydrogen atom.

Examples of the aforementioned heterocyclic substituent may include, but are not limited to, a phthalimide-derived substituent, a thiophene-derived substituent, a thiazole-derived substituent, a carbazole-derived substituent, and an imidazole-derived substituent.

The block copolymer of the present application may contain one or more among the aforementioned group of block 2, in addition to the aforementioned block 1. In this case, the number of blocks contained in the block copolymer may be 2, 3, or more. For example, the block copolymer may be a diblock copolymer that contains any one of the aforementioned blocks 1 plus any one among the aforementioned group of block 2.

The above block copolymer can basically exhibit excellent phase separation or an excellent self-assembling property. The phase separation or self-assembling property can be further improved by selecting each block and combining the blocks suitably, and satisfying one or more parameters that will be described below.

A block copolymer contains 2 or more polymer chains which are connected to one another by a covalent bond(s), and thus phase separation occurs. The block copolymer of the present application exhibits a phase separation property and, if needed, can form a nanoscale structure through microphase separation. The form and size of such a nanostructure may be controlled by the size (molecular weight or the like) of the block copolymer or relative ratios among the blocks. Examples of a structure that can be formed through phase separation may include a sphere, a cylinder, a gyroid, a lamella and an inverted structure, and the block copolymer's ability to form such a structure may be referred to as "self-assembling". The block copolymer of the present application may satisfy any one of the parameters that will be described below, or it may satisfy 2 or more parameters at the same time. In the present application, the term "vertical orientation" refers to the direction in which a block copolymer is oriented and may indicate that the nanostructure formed by the block copolymer is oriented vertically to the direction of a substrate. Technology for controlling the self-assembled structure of a block copolymer either horizontally or vertically on a variety of substrates accounts for a remarkably large part in a practical application of block copolymers. The orientation of a nanostructure in a block copolymer film is generally determined by which block among the blocks constituting the block copolymer is exposed either to the surface or in the air. In general, the majority of substrates are polar and the air is nonpolar; therefore, the blocks having higher polarities among the blocks that constitute a block copolymer are seen as wetting a substrate, and the blocks having lower polarities are seen as wetting the interface with the air. Therefore, there are a variety of techniques proposed to enable different types of blocks, each with distinct properties, of a block copolymer wetting at the substrate side simultaneously, the most representative of all is to produce a neutral surface to control the orientation. However, in one aspect of the present application, when the parameters below are properly controlled, a block polymer can be vertically oriented also on a substrate that had not been previously treated by any method, such as a surface neutralization, that is well-known in the art to achieve vertical orientation. Also, in another aspect of the present application, vertical orientation as the above can be induced within a short time over a large area through thermal annealing.

The block copolymer of one aspect of the present application can form a film, that produces an in-plane diffraction pattern on a hydrophobic surface during grazing-incidence small-angle X-ray scattering (GISAXS). The above block copolymer can form a film that produces an in-plane diffraction pattern on a hydrophilic surface during GISAXS.

In the present application, producing an in-plane diffraction pattern during GISAXS may refer to showing peaks that are vertical to the x-component in a GISAXS diffraction pattern during GISAXS analysis. Such peaks are observed due to vertical orientation of a block copolymer. Therefore, a block copolymer producing an in-plane diffraction pattern indicates vertical orientation. In another example, the number of the aforementioned peaks that are observed on the x-component of a GISAXS diffraction pattern may be at least 2, and when multiple peaks are present, the scattering vectors (q values) of the peaks may be observed to have integer ratios, in which case, the phase separation efficiency of the block copolymer can be further improved.

In the present application, errors are accounted for in the term "vertical"; for example, the definition of this term may include an error within the range of ±10 degrees, ±8 degrees, ±6 degrees, ±4 degrees, or ±2 degrees.

The block copolymer capable of forming a film that produces an in-plane diffraction pattern both on a hydrophilic surface and a hydrophobic surface—can exhibit vertical orientation on a variety of surfaces that had not been previously treated by any particular method to induce vertical orientation. In the present application, the term "a hydrophilic surface" refers to a surface whose wetting angle against purified water is in the range of 5 degrees to 20 degrees. Examples of a hydrophilic surface may include, but are not limited to, the surface of silicon that is surface-treated with oxygen plasma, sulfuric acid or a piranha solution. In the present application, the term "a hydrophobic surface" refers to a surface whose room-temperature wetting angle against purified water is in the range of 50 degrees to 70 degrees. Examples of a hydrophobic surface may include, but are not limited to, the surface of polydimethylsiloxane (PDMS) that is surface-treated with oxygen plasma, the surface of silicon that is surface-treated with hexamethyldisilazane (HMDS), and the surface of silicon that is surface treated with hydrogen fluoride (HF).

Unless specifically indicated otherwise, the properties (e.g. a wetting angle)—that may change depending on the temperature—in the present application are numerical values that are measured at room temperature. The term "room temperature" refers to the temperature in its natural state, which has not undergone heating or cooling, and may refer to a temperature of about 10° C. to 30° C., about 25° C., or about 23° C.

The film that is formed on a hydrophilic or hydrophobic surface and produces an in-plane diffraction pattern during GISAXS may be a film that has undergone thermal annealing. The film for a GISAXS measurement may be formed, for example, by applying a solution—that is prepared by dissolving the above block copolymer at a concentration of about 0.7 wt % in a solvent (e.g. fluorobenzene)—on the corresponding hydrophilic or hydrophobic surface at a thickness of about 25 nm and a coating area of 2.25 cm$^2$ (width: 1.5 cm, length: 1.5 cm) and thermal-annealing the coated layer. The thermal annealing may be carried out, for example, by allowing the above film to stand at a temperature of about 160° C. for about 1 hour. GISAXS may be measured by having an X-ray incident on a film, which is prepared in the aforementioned manner, at an angle of incidence in the range of about 0.12 to 0.23 degrees. A diffraction pattern that is scattered from the film can be obtained by a measuring device (e.g. 2D marCCD) that is well-known in the art. The method of using the diffraction pattern to verify the presence or absence of an in-plane diffraction pattern is well-known in the art.

The block copolymer that is observed to have the aforementioned peak during GISAXS can exhibit an excellent self-assembling property, which can also be controlled effectively depending on the purpose.

The block copolymer of the present application can show at least one peak within a predetermined scattering vector q range during X-ray diffraction (XRD) analysis.

For example, the above block copolymer may have at least one peak in the scattering vector q range of 0.5 $nm^{-1}$ to 10 $nm^{-1}$ during XRD analysis. In another example, the scattering vector q at which the above peak(s) appear(s) may be 0.7 $nm^{-1}$ or more, 0.9 $nm^{-1}$ or more, 1.1 $nm^{-1}$ or more, 1.3 $nm^{-1}$ or more, or 1.5 $nm^{-1}$ or more. Also, in another example, the scattering vector q at which the above peak(s) appear(s) may be 9 $nm^{-1}$ or less, 8 $nm^{-1}$ or less, 7 $nm^{-1}$ or less, 6 $nm^{-1}$ or less, 5 $nm^{-1}$ or less, 4 $nm^{-1}$ or less, 3.5 $nm^{-1}$ or less, or 3 $nm^{-1}$ or less.

The full width at half maximum (FWHM) of the peak(s) that is/are observed within the above scattering vector q range may be in the range of 0.2 to 0.9 $nm^{-1}$. In another example, the above FWHM may be 0.25 $nm^{-1}$ or more, 0.3 $nm^{-1}$ or more, or 0.4 $nm^{-1}$ or more. Also, in another example, the above FWHM may be 0.85 $nm^{-1}$ or less, 0.8 $nm^{-1}$ or less, or 0.75 $nm^{-1}$ or less.

In the present application, the term "FWHM" may refer to the width (i.e. the difference between the two extreme scattering vector q values) of the largest peak at half the maximum amplitude.

The above scattering vector q and FWHM in XRD analysis are numerical values obtained by a numerical analytical method that applies least-squares regression on the XRD analytical result. In the above method, the part that corresponds to the minimum intensity in an XRD diffraction pattern is set as the baseline and the minimum intensity is set as zero, then the peak profile of the above XRD pattern is subject to Gaussian fitting, and the aforementioned scattering vector q and FWHM are obtained from the fitted result. When the above Gaussian fitting is performed, the R-square value is at least 0.9 or more, 0.92 or more, 0.94 or more, or 0.96 or more. The method of obtaining the information from XRD analysis, as mentioned above, is well-known in the art; for example, a numerical analysis program, such as Origin, may be used.

The block copolymer that produces a peak that has the aforementioned FWHM value in the aforementioned scattering vector q range can have a crystalline region that is suitable for self-assembly. The block copolymer that is identified in the aforementioned scattering vector q range can exhibit an excellent self-assembling property.

XRD analysis may be carried out by transmitting X-rays through a block copolymer specimen and then measuring the scattering intensity with respect to a scattering vector. XRD analysis may be carried out on a block copolymer without requiring any particular pretreatment; for example, it may be conducted by drying the block copolymer under a suitable condition and then transmitting X-rays through it. An X-ray whose vertical size is 0.023 mm and horizontal size is 0.3 mm may be used. The scattering vector and FWHM may be obtained through the acquisition of the 2D diffraction pattern—that is scattered from the specimen—in the form of an image by using a measuring device (e.g. 2D marCCD) and the fitting of the acquired diffraction pattern in the aforementioned method.

When at least one among the blocks that constitute a block copolymer contains the aforementioned chain as will be described below, the number n of the chain-forming atoms in the chain may satisfy both the scattering vector q, which is obtained from the aforementioned XRD analysis, and the following Equation 1.

$$3 \text{ nm}^{-1} \text{ to } 5 \text{ nm}^{-1} = nq/(2\times\pi) \quad \text{[Equation 1]}$$

In Equation 1, n represents the number of the aforementioned chain-forming atoms, and q represents the smallest scattering vector whose peak is detectable, or the scattering vector that is observed to have the peak with the largest peak area, during the XRD analysis on the above block copolymer. In addition, π represents the ratio of the circumference of a circle to its diameter in Equation 1.

The q and the like that are introduced to the above Equation 1 are numerical values that are obtained in the same manner as the description of the aforementioned XRD analysis method.

The q and the like of Equation 1 may be, for example, a scattering vector in the range of 0.5 $nm^{-1}$ to 10 $nm^{-1}$. In another example, the q of Equation 1 may be 0.7 $nm^{-1}$ or more, 0.9 $nm^{-1}$ or more, 1.1 $nm^{-1}$ or more, 1.3 $nm^{-1}$ or more, or 1.5 $nm^{-1}$ or more. Also, in another example, the q of Equation 1 may be 9 $nm^{-1}$ or less, 8 $nm^{-1}$ or less, 7 $nm^{-1}$ or less, 6 $nm^{-1}$ or less, 5 $nm^{-1}$ or less, 4 $nm^{-1}$ or less, 3.5 $nm^{-1}$ or less, or 3 $nm^{-1}$ or less.

Equation 1 describes the relationship of the distance D among the blocks (each of which contains the aforementioned chain) with the number of chain-forming atoms, when a block copolymer is self-assembled to form a phase-separated structure. When the number of chain-forming atoms in the block copolymer containing the aforementioned chain satisfies Equation 1, the crystallinity of the chain increases, and thereby the phase separation or vertical orientation property can significantly improve. In another example, $nq/(2\times\pi)$ in Equation 1 may be 4.5 $nm^{-1}$ or less. In the above description, the distance (D, in the unit of nm) among the blocks containing the above chain can be calculated by using the equation, $D=2\times\pi/q$, where D represents the above distance (D, in the unit of nm) among the blocks, and π and q are as defined in Equation 1.

In one aspect of the present application, the absolute value of the difference between the surface energy of the block 1 and the surface energy of the block 2 in a block copolymer may be 10 mN/m or less, 9 mN/m or less, 8 mN/m or less, 7.5 mN/m or less, or 7 mN/m or less. Also, the absolute value of the difference between the above surface energies may be 1.5 mN/m, 2 mN/m, or 2.5 mN/m or more. The structure in which the block 1 and block 2, which have an absolute value of the difference in surface energies in the above range, are connected to each other by covalent bonds can induce microphase separation as the result of phase separation due to a sufficient level of immiscibility. In the above description, the block 1 may be, for example, the aforementioned block that contains the aforementioned chain.

A surface energy may be measured by using the Drop Shape Analyzer DSA100 (manufactured by KRUSS GmbH). Specifically, the surface energy may be measured on the film prepared by applying a coating solution—which is prepared by dissolving the subject specimen to be measured (i.e. a block copolymer or a homopolymer) in fluorobenzene to a solid concentration of about 2 wt %—on a substrate at a thickness of about 50 nm and a coating area of 4 $cm^2$ (width: 2 cm, length: 2 cm), drying at room temperature for about 1 hour, and then thermal-annealing at 160° C. for about 1 hour. The process of measuring a contact angle by dropping deionized water, whose surface tension is well-known in the art, on the above thermal-annealed film is repeated for 5 times, and the 5 measured values of a contact angle are averaged. Similarly, the process of measuring a contact angle by dropping diiodomethane, whose surface tension is well-known in the art, on the above thermal-annealed film is repeated for 5 times, and the 5 measured values of a contact angle are averaged. Subsequently, the surface energies can be obtained by using the averaged values of the contact angle, which were measured respectively with deionized water and diiodomethane, and substituting the numerical value (Strom value) that corresponds to the surface tension of a solvent into the equations according to the Owens-Wendt-Rabel-Kaelble method. The numerical value that corresponds to the surface energy of each block of a block copolymer can be obtained by using the above-described method on a homopolymer that is made up only of the monomer that constitutes the above block.

In the case that the block copolymer contains the aforementioned chain, the block that contains the chain may have a higher surface energy compared to the other block. For example, when the block 1 of a block copolymer contains the above chain, the surface energy of the block 1 may be higher than that of the block 2. In this case, the surface energy of the block 1 may be in the range of about 20 mN/m to 40 mN/m. The surface energy of the above block 1 may be 22 mN/m or more, 24 mN/m or more, 26 mN/m or more, or 28 mN/m or more. Also, the surface energy of the above block 1 may be 38 mN/m or less, 36 mN/m or less, 34 mN/m or less, or 32 mN/m or less. The block copolymer in which the above block 1 is contained and has a surface energy that is different from that of the block 2 as described above can exhibit an excellent self-assembling property.

In a block copolymer, the absolute value of the difference in densities of the block 1 and block 2 may be 0.25 g/cm$^3$ or more, 0.3 g/cm$^3$ or more, 0.35 g/cm$^3$ or more, 0.4 g/cm$^3$ or more, or 0.45 g/cm$^3$ or more. The aforementioned absolute value of the difference in densities may be 0.9 g/cm$^3$ or more, 0.8 g/cm$^3$ or less, 0.7 g/cm$^3$ or less, 0.65 g/cm$^3$ or less, or 0.6 g/cm$^3$ or less. The structure in which the block 1 and block 2 have the absolute value of the difference in densities within the above range and are connected to each other by covalent bonds may induce effective microphase separation as the result of phase separation due to a sufficient level of immiscibility.

The density of each block in the above block copolymer can be measured by using a buoyancy method that is well-known in the art; for example, the density can be measured by analyzing the mass of the block copolymer in a solvent, such as ethanol, whose mass and density in the air are known.

When a block copolymer contains the aforementioned chain, the block in which the chain is contained may have a lower density compared to the other block(s). For example, when the block 1 of a block copolymer contains the aforementioned chain, the density of the block 1 may be lower than that of the block 2. In this case, the density of the block 1 may be in the range of about 0.9 g/cm$^3$ to 1.5 g/cm$^3$. The density of the above block 1 may be 0.95 g/cm$^3$ or more. The density of the above block 1 may be 1.4 g/cm$^3$ or less, 1.3 g/cm$^3$ or less, 1.2 g/cm$^3$ or less, 1.1 g/cm$^3$ or less, or 1.05 g/cm$^3$ or less. The block copolymer in which the above block 1 is contained and has a density that is different from that of the block 2 as described above can exhibit an excellent self-assembling property. The aforementioned surface energy and density may be numerical values that are measured at room temperature.

A block copolymer may contain a block whose volume fraction is in the range of 0.4 to 0.8 and a block whose volume fraction is in the range of 0.2 to 0.6. In the case that the block copolymer contains the aforementioned chain, the volume fraction of the block in which the chain is contained may be in the range of 0.4 to 0.8. For example, when the chain is contained in the block 1, the volume fraction of the block 1 may be in the range of 0.4 to 0.8, and the volume fraction of the block 2 may be in the range of 0.2 to 0.6. The sum of volume fractions of the block 1 and block 2 may be equal to 1. The block copolymer that contains each block in the aforementioned volume fraction can exhibit an excellent self-assembling property. The volume fraction of each block in a block copolymer can be obtained based on the density of the block plus the molecular weight, which is measured by gel permeation chromatography (GPC).

The number average molecular weight (Mn) of a block copolymer may be, for example, in the range of 3,000 to 300,000. In the present specification, the term "number average molecular weight" refers to a numerical value that is measured with GPC and calibrated based on a standard polystyrene, and, unless specifically indicated otherwise, the term "molecular weight" in the present specification refers to number average molecular weight. In another example, Mn may be, for example, 3000 or more, 5000 or more, 7000 or more, 9000 or more, 11000 or more, 13000 or more, or 15000 or more. In still another example, Mn may be about 250000 or less, 200000 or less, 180000 or less, 160000 or less, 140000 or less, 120000 or less, 100000 or less, 90000 or less, 80000 or less, 70000 or less, 60000 or less, 50000 or less, 40000 or less, 30000 or less, or 25000 or less. A block copolymer may have a polydispersity (Mw/Mn) in the range of 1.01 to 1.60. In another example, the Mw/Mn may be about 1.1 or more, about 1.2 or more, about 1.3 or more, or about 1.4 or more.

In such a range, a block copolymer can exhibit a sufficient self-assembling property. The Mn and the like of a block copolymer can be adjusted in consideration of the self-assembled structure of interest and the like.

In the case that the block copolymer contains at least the aforementioned block 1 and block 2, the proportion of the block 1 (e.g. the proportion of the block that contains the aforementioned chain) in the above block copolymer may be in the range of 10 mol % to 90 mol %.

The present application is also related to a polymer film that contains the aforementioned block copolymer. The polymer film may be used in a variety of applications, for example, in a variety of electronic or electrical devices, in the process of forming the aforementioned patterns, in magnetic storage recording media such as flash memory, or in biosensors.

In one example, the aforementioned block copolymer may be realizing a regular structure, such as a sphere, a cylinder, a gyroid or a lamella, through self-assembly in the aforementioned polymer film.

For example, the block 1, the block 2 or (in the segment of another block that is covalently bonded to any of the block 1 and block 2) the segment may form a regular structure such as a lamella form or a cylindrical form in a block copolymer.

The above polymer film in the present application may have an in-plane diffraction pattern, which is a peak(s) vertical to the x-component of a GISAXS diffraction pattern, during GISAXS analysis. In another example, the number of the peaks observed on the x-component of the above GISAXS diffraction pattern may be at least 2 and, when there are multiple peaks present, the scattering vector q values of the peaks may be observed to be in an integer ratio.

In the present application, there is no particular limitation to the detailed method of preparing a block copolymer such as the above, as long as the method includes forming at least one block of the block copolymer by using monomers that can form each of the aforementioned structural unit. For example, a block copolymer may be prepared in a living radical polymerization (LRP) method that makes use of the above monomers. Examples of the methods include synthesis by anionic polymerization in which an organic rare-earth metal complex or organic alkali metal compound is used as the polymerization initiator in the presence of an alkali metal and an inorganic acid salt such as an alkaline earth metal; synthesis by an anionic polymerization method in which an organic alkali metal compound is used as the polymerization initiator in the presence of an organic aluminum compound; an atom transfer radical polymerization (ATRP) method in which an ATRP agent is used as the polymerization-control agent; an activators regenerated by electron transfer (ARGET) ATRP method in which an ATRP agent is used as the polymerization-control agent but the polymerization takes place in the presence of an organic or inorganic reducing agent that generates an electron; an initiators for continuous activator regeneration (ICAR) ATRP method; polymerization by a reversible addition-fragmentation chain transfer (RAFT) method in which an inorganic reducing agent and a RAFT agent are used; and a method of using an organic tellurium compound as the initiator, among which a suitable method may be selected for use.

For example, the aforementioned block copolymer may be prepared through a polymerization of a reactant (that includes the monomers capable of forming the aforementioned block) by a living radical polymerization method in the presence of a radical initiator and a living radical polymerization reagent.

There is no particular limitation to the method of forming another block to be contained in a block copolymer together with the block(s) formed of the aforementioned monomers during the preparation of the block copolymer; the monomer(s) may be suitably selected in consideration of the block type of interest for the formation of the other block.

The process of preparing a block copolymer may further include, for example, precipitating, in a nonsolvent, the polymerization product that is produced through the above processes.

There is no particular limitation to the type of the radical initiator, and the radical initiator may be suitably selected in consideration of the polymerization efficiency; for example, an azo compound such as azobisisobutyronitrile (AIBN) and 2,2'-azobis-(2,4-dimethylvaleronitrile), or a peroxide series such as benzoyl peroxide (BPO) and di-t-butyl peroxide (DTBP) may be used.

A living radical polymerization process may be carried out, for example, in a solvent such as methylene chloride, 1,2-dichloroethane, chlorobenzene, dichlorobenzene, benzene, toluene, acetone, chloroform, tetrahydrofuran, dioxane, monoglyme, diglyme, dimethylformamide, dimethyl sulfoxide, and dimethylacetamide.

Examples of a nonsolvent include, but are not limited to, an alcohol (such as methanol, ethanol, n-propanol, and isopropanol), a glycol (such as ethylene glycol), n-hexane, cyclohexane, n-heptane, and an ether (such as petroleum ether).

The present application is also related to a method of forming a polymer film by using the aforementioned block copolymer. The method may include forming a polymer film containing the above block copolymer on a substrate in a self-assembled state. For example, the above method may include forming a layer of the above block copolymer or a layer of a coating solution in which the block copolymer is dissolved in a suitable solvent, on a substrate by deposition or the like, and, if needed, it may also include a process of annealing or heat-treating the above layer.

The above annealing or heat-treating (heat-treatment) may be carried out, for example, based on the phase transition temperature or glass transition temperature of the block copolymer; for example, it may be carried out at a temperature equal to or greater than the above glass transition temperature or phase transition temperature. The duration of such a heat-treatment is not particularly limited and may be, for example, in the range of about 1 minute to 72 hours, although it may be subject to a change as necessary. Also, the heat-treatment temperature may be, for example, about 100° C. to 250° C., which may be subject to a change depending on the block copolymer to be used.

In another example, the layer that is formed as the above may be solvent-annealed in a room-temperature nonpolar solvent and/or polar solvent for about 1 minute to 72 hours.

The present application is also related to a method of forming a pattern. The above method may include, for example, a process of selectively removing the block 1 or block 2 of a block copolymer from the laminate that is made up of a substrate and a polymer film, which is formed on the substrate and contains the above self-assembled block copolymer. The above method may be a method of forming a pattern on the above substrate. For example, the above method may include forming, on a substrate, a polymer film that contains the above block copolymer, selectively removing any one or more blocks of the block copolymer that is present in the above film, and subsequently etching the substrate. The above method enables the formation of a micropattern, for example, in a nanoscale. Also, a variety of patterns such as a nanorod and a nanohole may be formed by the above method, depending on the structure of the block copolymer in the polymer film. If needed, the above block copolymer may be mixed with another copolymer, a homopolymer or the like for the formation of patterns. The type of the substrate to be applied in the above method is not particularly limited and may be selected to suit the application; for example, a silicon oxide may be used.

For example, the above method may form a silicon-oxide nanoscale pattern that exhibits a high aspect ratio. A variety of forms such as a nanorod and a nanohole may be realized, for example, by forming the above polymer film on a silicon oxide, selectively removing any one block of a block copolymer in the above polymer film where the block copolymer constitutes a predetermined structure, and then etching the silicone oxide by any one of various techniques, for example, by reactive-ion etching. Also, the above method may enable the realization of a nanopattern having a high aspect ratio.

For example, the above pattern may be realized in the scale of tens of nanometers, and such a pattern may be used for a variety of applications including, for example, magnetic recording media for the next-generation information and electronics.

For example, a pattern in which nanostructures (e.g. nanowires) whose width is about 3 nm to 40 nm are arranged spaced apart (e.g. by 6 nm to 80 nm) can be formed by the above method. In another example, a structure in which nanoholes whose width (e.g. diameter) is about 3 nm to 40 nm are arranged spaced apart by about 6 nm to 80 nm can also be realized.

In addition, the nanowires or nanoholes in the above structure can be made to have high aspect ratios.

In the above method, there is no particular limitation to the method of selectively removing any one block of a block copolymer; for example, a method of removing a relatively soft block by having the polymer film irradiated with suitable electromagnetic waves such as ultraviolet rays may be used. In this case, the condition of an ultraviolet ray irradiation is determined by the type of blocks in the block copolymer; for example, it may include an irradiation of the ultraviolet rays whose wavelength is about 254 nm for 1 minute to 60 minutes.

Following the ultraviolet ray irradiation, the process of additionally removing the segment that was previously disintegrated by ultraviolet rays may be carried out by treating the polymer film with an acid or the like.

In addition, there is no particular limitation to the process of etching the substrate by using, as the mask, the polymer film that has been selectively removed of certain blocks; for example, the above etching may be carried out through a reactive-ion etching with $CF_4$/Ar ions or the like. The above etching may be followed by the process of removing the polymer film from the substrate through an oxygen plasma treatment or the like.

BRIEF DESCRIPTION OF THE DRAWINGS

Each of FIGS. 1 and 2 is respectively an AFM image and SEM image of a film that is formed by using the block copolymer of Example 2.

EFFECT

Figure 1:
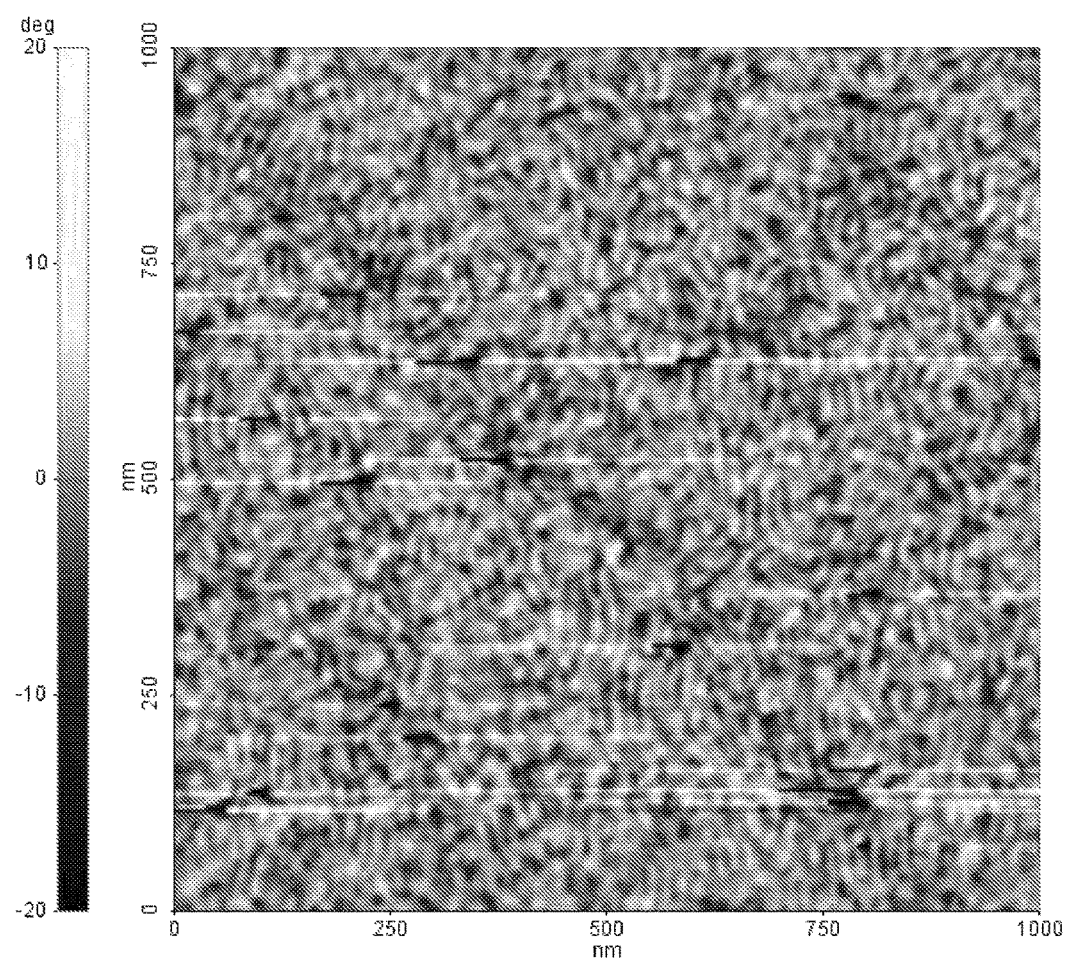

The present application can provide a block copolymer and uses thereof. The block copolymer of the present application exhibits an excellent self-assembling property or phase separation property and can be provided with a variety of required functions without constraint.

DETAILED DESCRIPTION OF EMBODIMENTS

The present application is described in more detail hereinafter through examples according to the present application, but the scope of the present application is not limited to the examples which are proposed hereinafter.

1. NMR Measurement

NMR analysis was carried out at room temperature by using a NMR spectrometer that includes a Varian Unity Inova (500 MHz) spectrometer with a 5-mm triple resonance probe. The analysis subject material was diluted with a solvent ($CDCl_3$) for an NMR measurement to a concentration of about 10 mg/ml for use, and the chemical shift was expressed in ppm.

Applied Abbreviations br=broad signal, s=singlet, d=doublet, dd=doublet of doublets, t=triplet, dt=doublet of triplets, q=quartet, p=quintet, m=multiplet.

2. Gel Permeation Chromatography (GPC)

The number average molecular weight (Mn) and molecular weight distribution were measured by GPC. The analysis subject material such as a macroinitiator or the block copolymer of the examples was put in a 5-mL vial and diluted with tetrahydrofuran (THF) to a concentration of about 1 mg/mL. Then, a standard specimen for calibration and the specimen to be analyzed were filtered with a syringe filter (pore size: 0.45 μm) and subsequently analyzed. ChemStation (Agilent Technologies Inc.) was used as the analytical program, each of the weight average molecular weight (Mw) and Mn was obtained by comparing the elution time of the specimen with the calibration curve, and then a molecular weight distribution (polydispersity index, PDI) was calculated as a ratio (Mw/Mn). The measuring condition of GPC is as follows:

<GPC Measuring Condition>

Device: 1200 Series of Agilent Technologies Inc.

Column: Two PLgel MIXED-B of Polymer Laboratories

Solvent: THF

Column temperature: 35° C.

Sample concentration: 1 mg/mL, 200 L is injected

Standard specimen: polystyrene (Mp: 3900000, 723000, 316500, 52200, 31400, 7200, 3940, 485)

Example 1

Synthesis of Monomer A

Monomer A that is represented by the following Structural Formula A—where R represents a methyl group, X represents —C(=O)—$X_1$—, $X_1$ represents an oxygen atom, Y represents a phenylene group that is substituted in the para position by a substituent (that is represented by -Q-P), Q represents —K—C(=O)—$X_2$—, K represents an ethylene group, $X_2$ represents an oxygen atom, and P represents a linear-chain hexyl group—was synthesized by the following method: p-coumaric acid (10 g), 1-hexanol (6.2 g) and p-toluenesulfonic acid (10.5 g) were put in a 100-mL flask containing 1,4-dioxane and allowed to react while refluxing at 105° C.; upon completion of the reaction, the reaction products were mixed with dichloromethane and removed of p-toluenesulfonic acid by a silica column; subsequently, the substances were purified in a silica column by using ethyl acetate with hexane and removed of the remaining 1-hexanol by distillation under reduced pressure to obtain a liquid p-coumaric acid hexyl (8.3 g, 55% yield).

<NMR Analysis Results>

$^1$H-NMR ($CDCl_3$): δ7.61 (d, 1H); δ7.41 (d, 2H); δ6.83 (d, 2H); δ6.28 (d, 1H); 5.47 (s, 1H); δ4.17 (t, 2H); δ1.68 (tt, 2H); δ1.38 (tt, 2H); δ1.31 (m, 4H); δ0.88 (t, 3H).

The above p-coumaric acid hexyl (8.3 g), methacrylic acid (3.2 g) and dichloromethane (300 mL) were introduced into a flask to which N,N'-dicyclohexylcarbodiimide (DCC, 7.6 g) and N,N-dimethylaminopyridine (DMAP, 1.6 g) were added and allowed to react. Upon completion of the reaction, the substances were removed of dichloromethane and then purified in a silica column by using ethyl acetate and hexane to obtain the liquid monomer A (9.6 g, 91% yield) that is represented by the following Structural Formula A.

<NMR Analysis Results>

$^1$H-NMR ($CDCl_3$): δ7.67 (d, 1H); δ7.55 (d, 2H); δ7.16 (d, 2H); δ6.41 (d, 1H); δ6.36 (s, 1H); δ5.78 (s, 1H); δ4.20 (t, 2H); δ2.06 (s, 3H); δ1.70 (tt, 2H); δ1.40 (tt, 2H); δ1.33 (m, 4H); δ0.91 (t, 3H).

[Structural Formula A]

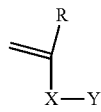

Synthesis of Polymer A

The above monomer A, a RAFT reagent (CPDB, 2-cyanoprop-2-yl-benzodithioate) and a thermal initiator (AIBN, azobisisobutyronitrile) were introduced into a flask in an equivalent ratio of 20:1:0.5 (monomer A:RAFT reagent: thermal initiator) and diluted with anisole to prepare a solution with a solid concentration of about 30 wt %. Subsequently, the prepared solution was allowed to react at about 70° C. for about 2 hours under a nitrogen atmosphere and, upon completion of the reaction, precipitated in methanol to obtain the polymer A. The $M_n$ and $M_w/M_n$ of the above polymer A were 8,100 and 1.35, respectively.

Example 2

Synthesis of Monomer B

Monomer B that is represented by Structural Formula A of Example 1—where R represents a methyl group, X represents —C(=O)—$X_1$—, $X_1$ represents an oxygen atom, Y represents phenylene that is substituted in the para position by a substituent (that is represented by -Q-P), Q represents a cyclohexylene group, P is a linear-chain pentyl group that is substituted for part of the above cyclohexylene group in the para position—was synthesized by the following method: 4-(trans-4-pentylcyclohexyl)phenol (15.0 g) and methacrylic acid (5.8 g) were introduced into a flask and dissolved in 400 mL of dichloromethane; dicyclohexylcarbodiimide (DCC) (13.8 g) and N,N-dimethylaminopyridine (DMAP) (3.0 g) were added to the prepared solution and allowed to react. Upon completion of the reaction, the reaction products were removed of dichloromethane, purified in a silica column by using ethyl acetate with hexane, and removed of the solvent to obtain the white solid monomer B (16.7 g, 87% yield).

<NMR Analysis Results>

$^1$H-NMR (CDCl$_3$): δ7.21 (d, 2H); δ7.02 (d, 2H); δ6.33 (s, 1H); δ5.73 (s, 1H); δ2.47 (t, 1H); δ2.06 (s, 3H); δ1.88 (t, 4H); 1.43 (q, 2H); δ1.33-1.21 (m, 8H); δ1.04 (q, 2H); δ0.90 (t, 3H)

Synthesis of Polymer B

The above monomer B, a RAFT reagent (CPDB) and a thermal initiator (AIBN) were introduced into a flask in an equivalent ratio of 15:1:0.1 (monomer B:RAFT reagent: thermal initiator) and diluted with anisole to prepare a solution with a solid concentration of about 22 wt %. Subsequently, the liquid mixture was allowed to react at about 70° C. for about 3 hours under a nitrogen atmosphere to obtain a macroinitiator. The above macroinitiator had $M_n$ and $M_w/M_n$ of 7,400 and 1.35, respectively, and showed a melting point of about 50° C. during DSC analysis.

The above macroinitiator, PFS (pentafluorostyrene) and a thermal initiator (AIBN) were mixed in a weight ratio of 1:500:0.5 (macroinitiator:PFS:AIBN) and diluted with anisole to prepare a solution with a solid concentration of about 70 wt %. Subsequently, the liquid mixture was allowed to react at about 70° C. for about 1 hour and 50 minutes under a nitrogen atmosphere to obtain the block copolymer B. The $M_n$ and $M_w/M_n$ of the above block copolymer B were 13,400 and 1.27, respectively.

Test Example 1

Figure 2:
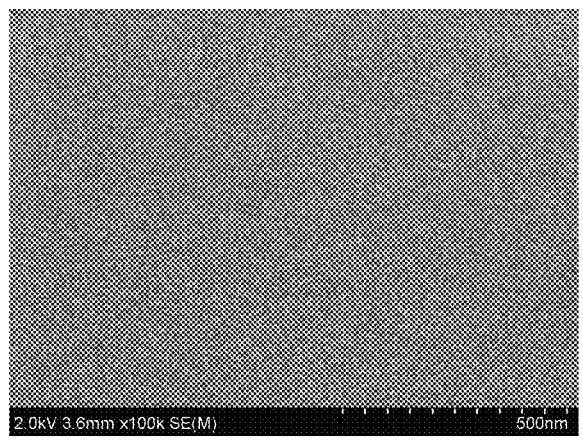

A self-assembled polymer film was formed by using the block copolymer B synthesized in Example 2 and the results were observed. Specifically, a coating solution that was prepared by dissolving a copolymer in a solvent to a concentration of about 1.0 wt % was spin-coated on a silicon wafer for about 60 seconds at a speed of about 3000 rpm, and the coated layer was thermal-annealed at about 220° C. to form a film that contains a self-assembled block copolymer. FIG. 1 is an AFM image of a polymer film that was formed in the above method, and FIG. 2 is an SEM image of the same film.

What is claimed is:

1. A block copolymer comprising a first block having a structural unit represented by Structural Formula 1 below:

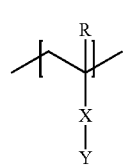

[Structural Formula 1]

wherein R represents a hydrogen atom or an alkyl group;

X represents an oxygen atom, a sulfur atom, —NR$_1$—, —S(=O)$_2$—, a carbonyl group, an alkylene group, an alkenylene group, an alkynylene group, —C(=O)—X$_1$— or —X$_1$—C(=O)—, wherein the X$_1$ represents a single bond, an oxygen atom, a sulfur atom, —NR$_1$—, —S(=O)$_2$—, an alkylene group, an alkenylene group or an alkynylene group, wherein the R$_1$ represents a hydrogen atom or an alkyl group; and Y represents an aryl group substituted with at least one of a substituent -Q-P, wherein the Q represents —K—C(=O)—X$_2$—, —X$_2$—C(=O)—K— or a cycloalkylene group, and the P represents a chain that contains 3 or more chain-forming atoms, wherein the X$_2$ represents an oxygen atom, a sulfur atom, —S(=O)$_2$—, an alkylene group, an alkenylene group or an alkynylene group, the K represents a linear or branched alkenylene group.

2. The block copolymer of claim 1, wherein the X of the Structural Formula 1 is —C(=O)—O— or —O—C(=O)—.

3. The block copolymer of claim 1, wherein the Y of the Structural Formula 1 is an aryl group with 6 to 12 carbons and is substituted in at least one part by the substituent -Q-P.

4. The block copolymer of claim 1, wherein the Y of the Structural Formula 1 is a phenyl group substituted with at least one part of the substituent -Q-P, wherein the substituent -Q-P is substituted in a para position (with respect to the X in the Structural Formula 1) of the phenyl group.

5. The block copolymer of claim 1, wherein the Q of the substituent -Q-P is —K—C(=O)—O— or —O—C(=O)—K—, wherein the K is an alkylene group with 2 to 20 carbons.

6. The block copolymer of claim 1, wherein the Q of the substituent -Q-P is a cycloalkylene group with 3 to 12 carbons.

7. The block copolymer of claim 1, wherein the P of the substituent -Q-P is an alkyl group with 3 to 30 carbons.

8. A block copolymer comprising a first block having a structural unit represented by Structural Formula 1 and a second block which has an aromatic structure that includes one or more halogen atoms

[Structural Formula 1]

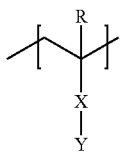

wherein R represents a hydrogen atom or an alkyl group; X represents a single bond, an oxygen atom, a sulfur atom, $-NR_1-$, $-S(=O)_2-$, a carbonyl group, an alkylene group, an alkenylene group, an alkynylene group, $-C(=O)-X_1-$ or $-X_1-C(=O)-$, wherein the $X_1$ represents a single bond, an oxygen atom, a sulfur atom, $-NR_1-$, $-S(=O)_2-$, an alkylene group, an alkenylene group or an alkynylene group, wherein the $R_1$ represents a hydrogen atom or an alkyl group; and Y represents an aryl group substituted with at least one of a substituent -Q-P, wherein the Q represents $-K-C(=O)-X_2-$, $-X_2-C(=O)-K-$ or a cycloalkylene group, and the P represents a chain that contains 3 or more chain-forming atoms, wherein the $X_2$ represents an oxygen atom, a sulfur atom, $-S(=O)_2-$, an alkylene group, an alkenylene group or an alkynylene group, the K represents an alkenylene group.

9. The block copolymer of claim 8, wherein the second block is represented by Structural Formula 2 below:

[Structural Formula 2]

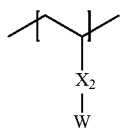

where in the Structural Formula 2, $X_2$ represents a single bond, an oxygen atom, a sulfur atom, $-S(=O)_2-$, an alkylene group, an alkenylene group, an alkynylene group, $-C(=O)-X_1-$ or $-X_1-C(=O)-$, wherein the $X_1$ represents a single bond, an oxygen atom, a sulfur atom, $-S(=O)_2-$, an alkylene group, an alkenylene group or an alkynylene group; and W represents an aryl group that includes at least one halogen atom.

10. The block copolymer of claim 8, wherein the second block is represented by Structural Formula 3 below:

[Structural Formula 3]

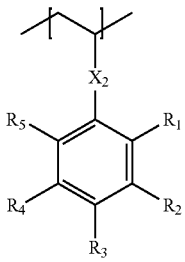

where in the Structural Formula 3, $X_2$ represents a single bond, an oxygen atom, a sulfur atom, $-S(=O)_2-$, an alkylene group, an alkenylene group, an alkynylene group, $-C(=O)-X_1-$ or $-X_1-C(=O)-$, wherein the $X_1$ represents a single bond, an oxygen atom, a sulfur atom, $-S(=O)_2-$, an alkylene group, an alkenylene group or an alkynylene group; and each of $R_1$ to $R_5$ independently represents a hydrogen atom, an alkyl group, a haloalkyl group or a halogen atom, wherein one or more halogen atoms are included in positions marked as $R_1$ to $R_5$.

11. The block copolymer of claim 10, wherein three or more halogen atoms are included in the positions marked as $R_1$ to $R_5$.

12. The block copolymer of claim 10, wherein five or more halogen atoms are included in the positions marked as $R_1$ to $R_5$.

13. The block copolymer of claim 8, wherein the halogen atom is a fluorine atom.

14. A polymer film comprising the block copolymer of claim 1, wherein the block copolymer of claim 1 is self-assembled.

15. A method of forming a polymer film, comprising:
forming the polymer film on a substrate, wherein the polymer film comprises the block copolymer of claim 1, wherein the block copolymer of claim 1 is self-assembled.

16. A method of forming a pattern, the method comprising:
selectively removing the first block or another block of the block copolymer of claim 1 from a laminate comprising a substrate and a polymer film that is formed on the substrate and includes the block copolymer of claim 1, wherein the block copolymer of claim 1 is self-assembled.

* * * * *